United States Patent
Soin et al.

(10) Patent No.: US 12,343,541 B2
(45) Date of Patent: *Jul. 1, 2025

(54) RAPID FREQUENCY CYCLING DURING ELECTRICAL STIMULATION

(71) Applicant: Soin Neuroscience, LLC, Dayton, OH (US)

(72) Inventors: Amol Soin, Dayton, OH (US); Eric A. Schepis, Alpharetta, GA (US)

(73) Assignee: Soin Neuroscience, LLC, Dayton, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/641,962

(22) Filed: Apr. 22, 2024

(65) Prior Publication Data

US 2025/0050105 A1    Feb. 13, 2025

Related U.S. Application Data

(63) Continuation of application No. 18/352,731, filed on Jul. 14, 2023, now Pat. No. 11,964,155.

(51) Int. Cl.
*A61N 1/36* (2006.01)
*A61N 1/05* (2006.01)

(52) U.S. Cl.
CPC ....... *A61N 1/36132* (2013.01); *A61N 1/0551* (2013.01); *A61N 1/36071* (2013.01);
(Continued)

(58) Field of Classification Search
CPC .............. A61N 1/36132; A61N 1/0551; A61N 1/36071; A61N 1/36146; A61N 1/36153;
(Continued)

(56) References Cited

U.S. PATENT DOCUMENTS 5,983,141 A    11/1999   Sluijter et al.
7,117,038 B1   10/2006   Overstreet
(Continued)

FOREIGN PATENT DOCUMENTS

CN    101390789 A    3/2009
CN    101583879 A    11/2009
(Continued)

OTHER PUBLICATIONS

International Search Report, International Searching Authority, International Patent Application No. PCT/US2024/037554, Aug. 5, 2024, 2 pages.
(Continued)

*Primary Examiner* — Paula J Stice
(74) *Attorney, Agent, or Firm* — Taft Stettinius & Hollister LLP

(57) ABSTRACT

A method of rapid frequency cycling during electrical stimulation according to an embodiment may include determining, by a controller of an electrical stimulation system, a plurality of frequency band groupings of discrete frequency bands of an electrical stimulation signal having a frequency range, wherein each frequency band grouping includes at least one discrete frequency band, wherein a corresponding current or voltage amplitude of the electrical stimulation signal is independently tuned within each discrete frequency band based on feedback received from a patient, determining, by the controller, a random sequence of the frequency band groupings of the plurality of frequency band groupings, generating, by at least one signal generator controlled by the controller, the electrical stimulation signal according to the determined random sequence of the frequency band groupings, and delivering the generated electrical stimulation signal through an electrode array to the patient to provide therapy to the patient.

20 Claims, 18 Drawing Sheets

(52) U.S. Cl.
CPC ..... *A61N 1/36146* (2013.01); *A61N 1/36153* (2013.01); *A61N 1/36157* (2013.01); *A61N 1/36171* (2013.01); *A61N 1/36185* (2013.01); *A61N 1/36196* (2013.01)

(58) Field of Classification Search
CPC ............ A61N 1/36157; A61N 1/36171; A61N 1/36185; A61N 1/36196
See application file for complete search history.

(56) References Cited

U.S. PATENT DOCUMENTS

| | | |
|---|---|---|
| 10,603,498 B2 | 3/2020 | Blum et al. |
| 2003/0114886 A1 | 6/2003 | Gluckman et al. |
| 2006/0149337 A1 | 7/2006 | John |
| 2006/0161235 A1 | 7/2006 | King |
| 2007/0027486 A1 | 2/2007 | Armstrong |
| 2007/0060991 A1 | 3/2007 | North et al. |
| 2007/0142864 A1 | 6/2007 | Libbus et al. |
| 2008/0077192 A1 | 3/2008 | Harry et al. |
| 2008/0269836 A1 | 10/2008 | Foffani et al. |
| 2009/0030476 A1 | 1/2009 | Hargrove |
| 2010/0010556 A1 | 1/2010 | Zhao et al. |
| 2011/0009919 A1 | 1/2011 | Carbunaru et al. |
| 2011/0009923 A1 | 1/2011 | Lee |
| 2011/0144521 A1 | 6/2011 | Molnar et al. |
| 2011/0201944 A1 | 8/2011 | Higgins et al. |
| 2012/0059438 A1 | 3/2012 | De Ridder |
| 2012/0123502 A1 | 5/2012 | Aghassian et al. |
| 2013/0245486 A1 | 9/2013 | Simon et al. |
| 2013/0253365 A1 | 9/2013 | Crosson et al. |
| 2013/0317564 A1 | 11/2013 | Lin et al. |
| 2014/0031895 A1 | 1/2014 | Rahimi et al. |
| 2014/0316268 A1 | 10/2014 | Kafiluddi et al. |
| 2015/0012063 A1 | 1/2015 | Chen |
| 2015/0157864 A1 | 6/2015 | Rosenberg |
| 2016/0001083 A1 | 1/2016 | Moffitt et al. |
| 2016/0199662 A1 | 7/2016 | Wundrich et al. |
| 2016/0256689 A1 | 9/2016 | Vallejo et al. |
| 2016/0271413 A1 | 9/2016 | Vallejo et al. |
| 2017/0001003 A1 | 1/2017 | Pivonka et al. |
| 2017/0106197 A1 | 4/2017 | Wechter et al. |
| 2019/0201657 A1 | 7/2019 | Popelka et al. |
| 2019/0298988 A1 | 10/2019 | Monteiro |
| 2019/0366097 A1 | 12/2019 | Schepis |
| 2020/0054879 A1 | 2/2020 | Torgerson |
| 2020/0139127 A1 | 5/2020 | Zhang et al. |
| 2020/0164213 A1 | 5/2020 | John |
| 2020/0353256 A1 | 11/2020 | Vallejo et al. |
| 2022/0080200 A1 | 3/2022 | Molnar et al. |
| 2022/0096822 A1 | 3/2022 | Schepis et al. |
| 2022/0257957 A1 | 8/2022 | Kotchevar et al. |
| 2022/0288394 A1 | 9/2022 | Bennett et al. |
| 2023/0074017 A1 | 3/2023 | Pan |
| 2023/0146551 A1 | 5/2023 | Park et al. |

FOREIGN PATENT DOCUMENTS

| | | |
|---|---|---|
| EP | 2703042 A1 | 3/2014 |
| JP | 2006204520 A | 8/2006 |
| JP | 2009505689 A | 2/2009 |
| WO | 9318821 A1 | 9/1993 |

OTHER PUBLICATIONS

Written Opinion of the International Searching Authority, International Searching Authority, International Patent Application No. PCT/US2024/037554, Aug. 5, 2024, 5 pages.

RAPID FREQUENCY CYCLING DURING ELECTRICAL STIMULATION

CROSS-REFERENCE TO RELATED APPLICATIONS

This application is a continuation of U.S. patent application Ser. No. 18/352,731, filed on Jul. 14, 2023, the contents of which are incorporated herein by reference in their entirety.

BACKGROUND

Electrical stimulation technologies are used to mitigate pain and other conditions. The technologies work by delivering electrical stimulation to the various parts of the nervous system (e.g., sensory receptors, peripheral nerves, spinal cord, and brain). For example, the stimulation devices used today deliver pulsed periodic waveforms through electrical contacts that are positioned overtop of the dorsal columns of the spinal cord, dorsal root ganglion, or long peripherals nerves. The electrical contacts that are used for stimulation are chosen at the onset of the treatment and maintained throughout the duration of the therapy, which may last for years. Although the technologies used today cause a moderate reduction in pain intensity in the majority of the persons treated, the effects of the stimulation often decline after a few years of use. This phenomenon is known as neurological tolerance (or accommodation), and it is the leading cause of stimulator removal. Electrical stimulation technologies are used to treat a variety of disease states, such as chronic pain, overactive bladder, movement disorders, and cardiovascular disease. However, the treatment effects and time-course are limited.

SUMMARY

One embodiment is directed to a unique system and method for rapid frequency cycling during electrical stimulation. Other embodiments are directed to apparatuses, systems, devices, hardware, methods, and combinations thereof for rapid frequency cycling during electrical stimulation.

According to an embodiment, a method of rapid frequency cycling during electrical stimulation may include determining, by a controller of an electrical stimulation system, a plurality of frequency band groupings of discrete frequency bands of an electrical stimulation signal having a frequency range, wherein each frequency band grouping of the plurality of frequency band groupings includes at least one discrete frequency band, wherein at least one of a corresponding current amplitude or a corresponding voltage amplitude of the electrical stimulation signal is independently tuned within each discrete frequency band based on feedback received from a patient, determining, by the controller, a random sequence of the frequency band groupings, generating, by at least one signal generator controlled by the controller, the electrical stimulation signal according to the determined random sequence of the frequency band groupings, and delivering the generated electrical stimulation signal through an electrode array to the patient to provide therapy to the patient.

In some embodiments, the plurality of frequency band groupings may consist of four frequency band groupings.

In some embodiments, the plurality of frequency band groupings may consist of five frequency band groupings.

In some embodiments, the electrical stimulation signal may include a periodic pulse wave.

In some embodiments, the method may further include determining, by the controller, a corresponding duration of delivery of the electrical stimulation signal within each frequency band grouping.

In some embodiments, generating the electrical stimulation signal may include generating the electrical stimulation signal according to the determined random sequence of the frequency band groupings and the determined corresponding duration of delivery of the electrical stimulation signal within each frequency band grouping.

In some embodiments, determining the random sequence of the frequency band groupings may include periodically determining a new random sequence of the frequency band groupings of the plurality of frequency band groupings, and generating the electrical stimulation signal may include generating the electrical stimulation signal according to the determined new random sequence of the frequency band groupings.

In some embodiments, one frequency band grouping of the plurality of frequency band groupings may be delimited by a lower frequency of 8 kHz and an upper frequency of 12 kHz.

In some embodiments, the frequency range may zero to 1500 Hz, and one frequency band grouping of the plurality of frequency band groupings may be delimited by a lower frequency of 400 Hz and an upper frequency of 900 Hz.

In some embodiments, one frequency band grouping of the plurality of frequency band groupings may be delimited by a lower frequency of 8 kHz and another frequency band grouping of the plurality of frequency band groupings may be delimited by an upper frequency no greater than 1500 Hz.

In some embodiments, the at least one of the current amplitude or the corresponding voltage amplitude of the electrical stimulation signal outside of the frequency range may be nominally zero.

In some embodiments, the method may include determining, by the controller, a random electrical configuration of the electrode array by randomly selecting a first set of electrical contacts of the electrode array to operate as cathodes and a second set of electrical contacts of the electrode array, different from the first set of electrical contacts, to operate as anodes, and delivering the electrical stimulation signal through the electrode array may include delivering the electrical stimulation signal to the patient using the random electrical configuration of the electrode array.

In some embodiments, determining the random sequence of the frequency band groupings of the plurality of frequency band groupings may include randomly selecting a predefined sequence of the frequency band groupings from a plurality of distinct predefined sequences of the frequency band groupings.

In some embodiments, the electrode array may be positioned such that a distal electrical contact of the electrode array stimulates the patient's thoracic spine at T8 and a proximal electrical contact of the electrode array stimulates the patient's vertebral body at T10 to treat the patient for intractable leg and back pain.

In some embodiments, the method may further include determining, by the controller, a patient-specific sensory threshold of the electrical stimulation signal for the patient, defining, by the controller, a maximum amplitude of the electrical stimulation signal based on the patient-specific sensory threshold, and independently tuning, by the controller, the at least one of the corresponding current amplitude or the corresponding voltage amplitude of the electrical stimulation signal within each discrete frequency band based on feedback received from the patient, where the patient adjusts the at least one of the corresponding current amplitude or the corresponding voltage amplitude of the electrical stimulation signal within each discrete frequency band to a patient-selected point between zero and the maximum amplitude based on a reduction in pain physically experienced by the patient in real time.

In some embodiments, determining the patient-specific sensor threshold of the electrical stimulation signal may include independently determining a corresponding patient-specific sensory threshold of the electrical stimulation signal for each discrete frequency band, and defining the maximum amplitude of the electrical stimulation signal may include defining a corresponding maximum amplitude for each discrete frequency band.

In some embodiments, defining the maximum amplitude of the electrical stimulation signal may include defining the maximum amplitude as approximately 110% of the patient-specific sensory threshold.

According to another embodiment, a method of rapid frequency cycling during electrical stimulation may include determining, by a controller of an electrical stimulation system, a plurality of frequency band groupings of discrete frequency bands of an electrical stimulation signal having a frequency range, wherein each frequency band grouping of the plurality of frequency band groupings includes at least one discrete frequency band, wherein at least one of a corresponding current amplitude or a corresponding voltage amplitude of the electrical stimulation signal is independently tuned within each discrete frequency band based on feedback received from a patient, determining, by the controller, a corresponding duration of delivery of the electrical stimulation signal within each frequency band grouping, determining, by the controller, a random electrical configuration of an electrode array of the electrical stimulation system by randomly selecting a first set of electrical contacts of the electrode array to operate as cathodes and a second set of electrical contacts of the electrode array, different from the first set of electrical contacts, to operate as anodes, determining, by the controller, a random sequence of the frequency band groupings, generating, by at least one signal generator controlled by the controller, the electrical stimulation signal according to the determined random sequence of the frequency band groupings and the determined corresponding duration of delivery of the electrical stimulation signal within each frequency band grouping, and delivering the generated electrical stimulation signal through the electrode array to the patient using the random electrical configuration of the electrode array to provide therapy to the patient.

In some embodiments, one frequency band grouping of the plurality of frequency band groupings may be delimited by a lower frequency of 8 kHz and an upper frequency of 12 kHz.

In some embodiments, the plurality of frequency band groupings may consist of one of four frequency band groupings or five frequency band groupings.

In some embodiments, the duration of delivery of the electrical stimulation signal within each frequency band grouping may be selected from a range of 0.1 milliseconds to 5 seconds.

In some embodiments, a pause duration between delivery of the electrical stimulation signal within two sequential frequency band groupings in a sequence may be 1 millisecond.

This summary is not intended to identify key or essential features of the claimed subject matter, nor is it intended to be used as an aid in limiting the scope of the claimed subject matter. Further embodiments, forms, features, and aspects of the present application shall become apparent from the description and figures provided herewith.

BRIEF DESCRIPTION OF THE DRAWINGS

The concepts described herein are illustrative by way of example and not by way of limitation in the accompanying figures. For simplicity and clarity of illustration, elements illustrated in the figures are not necessarily drawn to scale. Where considered appropriate, references labels have been repeated among the figures to indicate corresponding or analogous elements.

DETAILED DESCRIPTION

Figure 1:
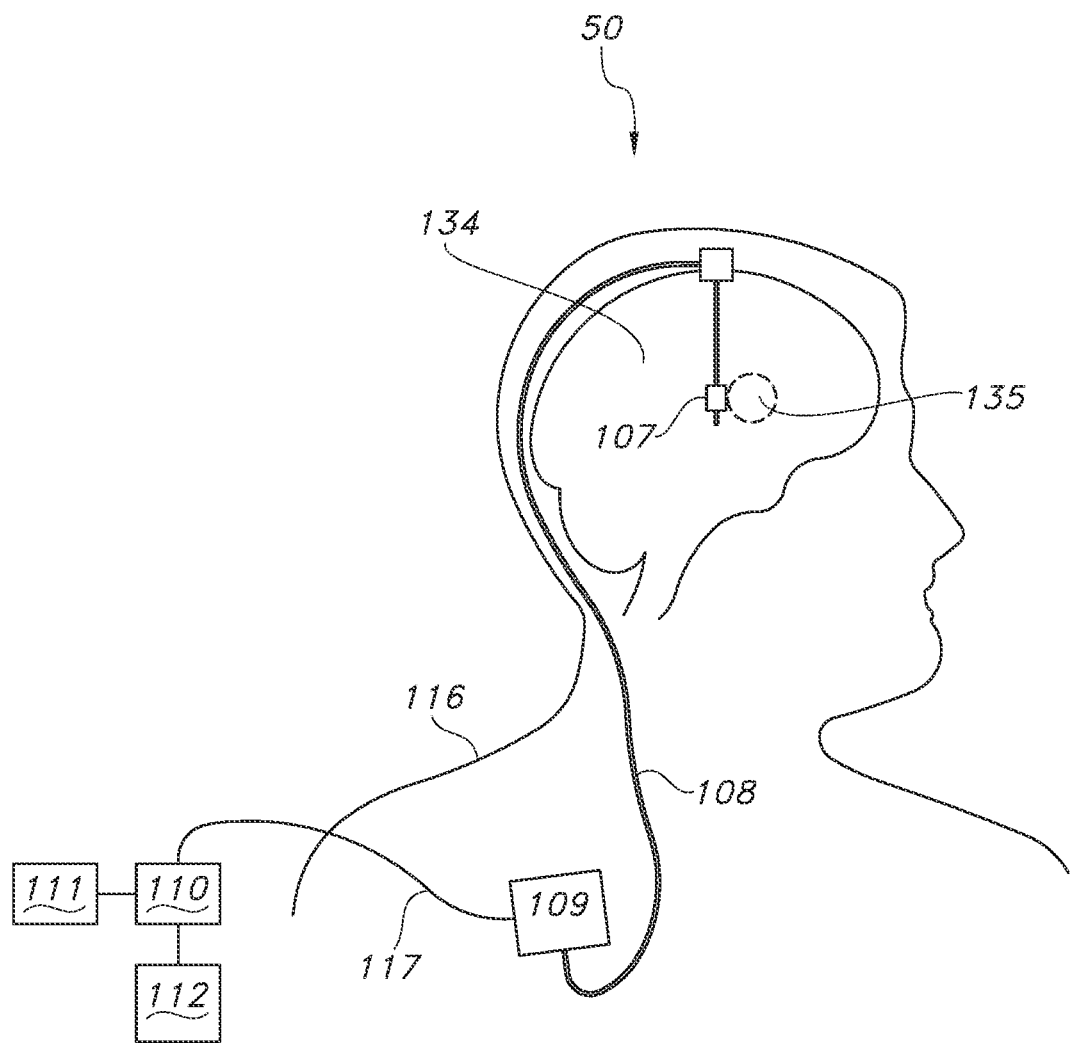
FIG. 1 illustrates at least one embodiment of a system for delivering one or more electrical signals to target neural tissue, non-neural tissue, or a combination thereof in a patient, where the target tissue is located within or adjacent to the patient's brain.

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

The disclosed embodiments may, in some cases, be implemented in hardware, firmware, software, or a combination thereof. The disclosed embodiments may also be implemented as instructions carried by or stored on one or more transitory or non-transitory machine-readable (e.g., computer-readable) storage media, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures unless indicated to the contrary. Additionally, the inclusion of a structural or method feature in a particular figure is not meant to imply that such feature is required in all embodiments and, in some embodiments, may not be included or may be combined with other features.

As described above, existing electrical stimulation technologies are inhibited from long-term efficacy due to the patient often developing neurological tolerance (or accommodation) to the stimulation. It should be appreciated that the technologies described herein include an electrical stimulation system that delivers electrical stimuli in manner that replicates aperiodic or pseudo-aperiodic signals through a set of electrodes (e.g., electrical contacts) to neural and/or non-neural tissue, which has been found to be more effective at treating acute and chronic pain and other medical disorders than existing technologies. For example, in some embodiments, the electrical stimulation system may randomly cycle periodic preprogrammed waveforms (e.g., patient-specific tuned) via pulse waves in rapid fashion such that the spinal cords "feels" or interprets the signal as being random, and therefore the patient is unable to develop neurological tolerance (or accommodation) to the stimulation. That is, the electrical stimulation system may randomly cycle to deliver aperiodic signaling to achieve maximum pain reduction in the patient. In some embodiments, this may entail using, for example, an 8-contact electrode array or lead and randomly switching between electrodes that are stimulated, and simultaneously randomly cycling between different frequency bands. Further, in some embodiments, the electrical field may be maximized by using the very top/distal electrodes and very bottom/proximal electrodes to deliver stimulation through as wide as area as possible (e.g., with the top electrode as an anode and the bottom electrode as a cathode, or vice versa).

As described in greater detail below, the therapy may be generated by an external or implantable electrical stimulator and delivered through electrodes (e.g., an electrode array) to the patient's brain or spinal cord, a dorsal root ganglion, a sympathetic nerve or chain ganglion, a cranial nerve, a parasympathetic nerve, or a peripheral nerve. The therapy may be used to treat pain (e.g., chronic pain), an autonomic disorder (e.g., diabetic peripheral neuropathy, hypertension, hypotension, complex regional pain syndrome (CRPS), Raynaud's syndrome, overactive bladder, urinary incontinence, fecal incontinence, fecal constipation, migraine, etc.), a sensory disorder (e.g., tinnitus, hearing loss, vertigo, etc.), a motor disorder (e.g., Huntington's disease, Parkinson's disease, Multiple Sclerosis, spinal muscular atrophy (SMA), dystonia, essential tremor, etc.), or a combination thereof. Further, the therapy provided to the patient can elicit plastic changes in neural tissue, non-neural tissue, or a combination thereof to mitigate or abolish a pathophysiologic disease or syndrome. Plastic changes are changes to the neural tissue, non-neural tissue, or a combination thereof in response to physiological demands. Such plastic changes can include morphological and functional changes.

It should be appreciated that electrical stimulation systems may use electrical pulses to modulate nervous tissue. Each pulse is defined by its amplitude, pulse duration, phase (e.g., monophasic, biphasic, shape), frequency (during pulse repetition), and overall time-course (inter-pulse and intrapulse time periods). Electrical stimulation devices may be equipped with multiple programs, where each program records and executes a stimulation pulse with a unique set of parameters that are selected by the user. However, the multiple programs are independent from each other and are not configured to play in any sequence, such as at the same time (simultaneously), sequentially or randomly. Instead, the user decides when to activate each program. Moreover, each pulse, regardless of the program, produces a fixed power spectrum (power vs. frequency). The spectral components produced by the programmed pulse cannot be adjusted to deliver a unique stimulation power at a chosen frequency or set of frequencies, which is needed for optimal therapeutic effects. Furthermore, the programmed pulse cannot be adjusted to deliver a unique power at a frequency or set of powers and frequencies that are stochastic.

It should be appreciated that the technologies described herein may involve an electrical stimulation system that is equipped to synthesize a composite waveform that is composed of one or more programs to deliver power at a discrete set of frequency bands selected by a user or the system (e.g., via artificial intelligence or machine learning) for optimal therapy. In various embodiments, each of the programs may be composed of periodic waveforms (e.g., pulses, sine waves, etc.), or aperiodic or pseudo periodic waveforms (e.g., white noise, impulses, etc.) and delivered simultaneously, sequentially, or randomly (or any combination thereof) to produce a composite waveform describing the spectral components selected by the user for optimal therapy. The programs may, for example, be additive, subtracted, convoluted, multiplied (e.g., gain), divided, collided, or filtered (or any combination thereof) to produce the composite signal. Moreover, the programs can be pre-programmed or determined in real-time depending on the particular embodiment. The electrical stimulation system may be capable of adding variability to the composite waveform's power, frequency, or combination thereof, of the chosen spectral components. The electrical stimulation system may further be capable of varying which electrical contacts are used to deliver the composite signal (e.g., based on electrical contact size, shape, location on the lead, or based on power or frequency, or degree of randomness). In some embodiments, the system's controller may be "smart" and used to orchestrate the various programs as necessary to deliver the composite signal with the user selected power spectra.

Referring now to FIG. 1, there is illustrated a system 50 for delivering one or more electrical signals to provide therapy to a patient 116, where the target neural tissue, non-neural tissue, or a combination thereof 135 is located within or adjacent tissue within the patient's brain 134. In general, the system 50 in FIG. 1 can include one or more electrodes 107 (shown diagrammatically in FIG. 1) that are connected by an electrical lead 108 to a signal generator 109. As described herein, multiple electrodes 107 may be arranged into an electrode array in some embodiments (see, e.g., FIG. 13). In various embodiments, one or more electrodes 107 (or electrical contacts) may be embodied on, form a portion of, or be electrically coupled to one or more electrical leads 108 that are electrically (or electromagnetically) coupled to the signal generator 109. An additional lead 117 can be used to couple the signal generator 109 to the rest of the system 50, which can include a user interface 112 and a controller 110, where it is to be understood that as an alternative to the use of the lead 117, the signal generator 109 can be wirelessly connected to the rest of the system 50. The system 50 can also include a power system 111 and/or a patient monitor system. Further, it should be understood that while the system 50 of FIG. 1 illustrates a configuration where electrical signals can be delivered to target neural tissue, non-neural tissue, or a combination 135 thereof utilizing one or more electrodes 107 (e.g., an electrode array) coupled to an implantable signal generator 109 via a lead 108, the electrode(s) 107 can alternatively be coupled to an external signal generator via a wireless antenna system. It should be appreciated that, in some embodiments, more than one electrode 107, more than one electrical lead 108, and/or more than one signal generator 109 may be used in the system 50. Regardless of the exact type (e.g., percutaneous, transcutaneous, implantable, etc.) or configuration (e.g., monopolar, bipolar, multipolar, etc.) of the electrode(s) 107, the electrode(s) 107 can be in the form of an electrode assembly that can deliver electrical signals to a patient to provide therapy to the patient and/or improve one or more of the patient's symptoms. Specific diseases or conditions that can be treated based on stimulation of the brain include, for example, Parkinson's disease, essential tremor, depression, obsessive compulsive disorder, Tourette's syndrome, epilepsy, schizophrenia, narcolepsy, seizures, Alzheimer's disease, tinnitus, Meniere's disease, and chronic pain.

Figure 2:
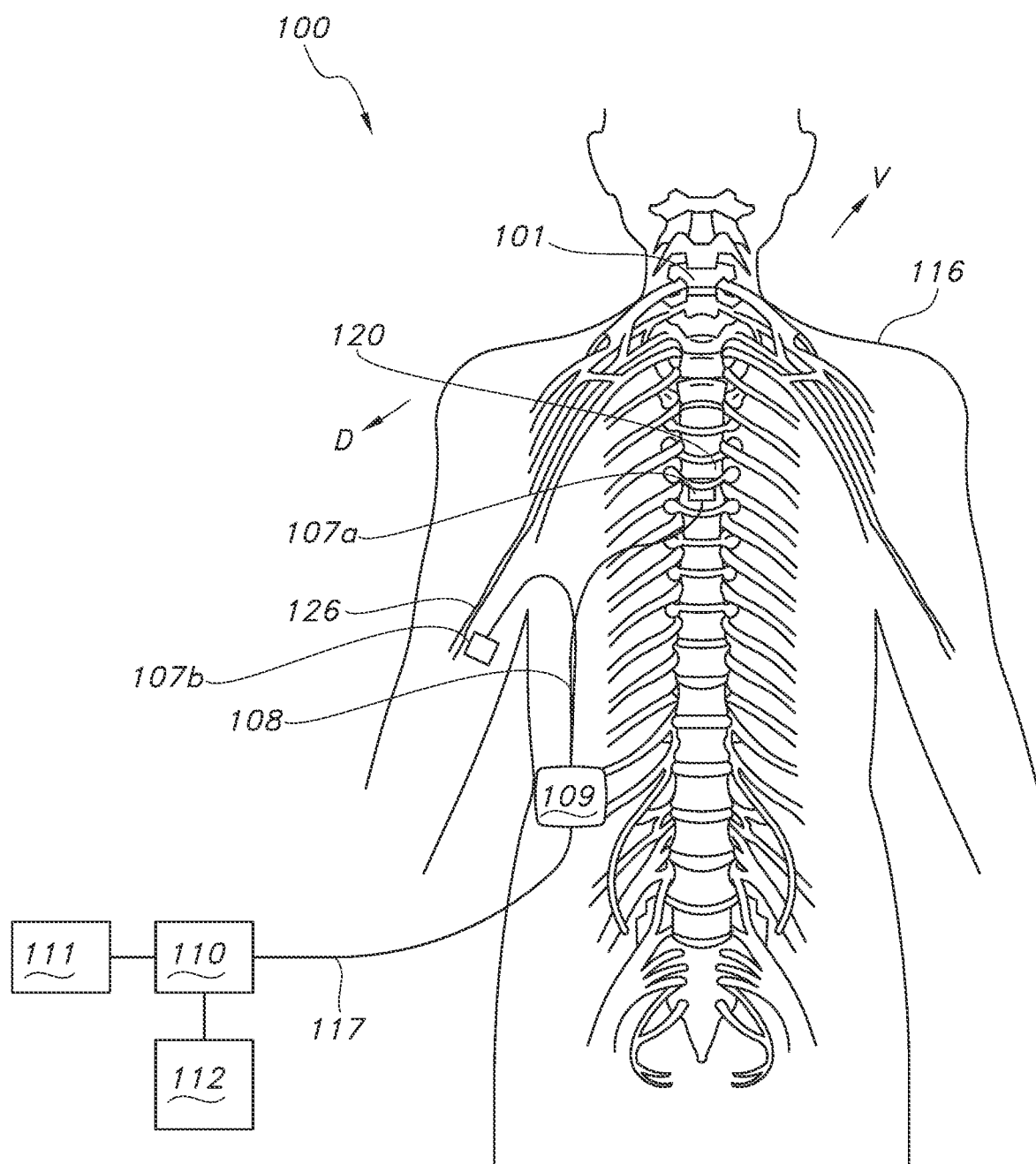
FIG. 2 illustrates at least one embodiment of a system for delivering one or more electrical signals to target neural tissue, non-neural tissue, or a combination thereof in a patient, where the target tissue is located within or adjacent the spinal cord.

Referring now to FIG. 2, there is illustrated a system 100 for delivering one or more electrical signals to provide therapy to a patient, where the target neural tissue, non-neural tissue, or a combination thereof is located within or adjacent the spinal cord 101 of a patient 116. As shown in FIG. 2, the system 100 can include multiple devices to control and deliver electrical signals to one or more areas of target neural tissue, non-neural tissue, or a combination thereof located within or adjacent the spinal cord 101 to provide therapy to a patient 116. In general, the system 100 in FIG. 2 can include one or more electrodes 107a and/or 107b that are connected by one or more electrical leads 108 to a signal generator 109. As described herein, multiple electrodes 107 may be arranged into an electrode array in some embodiments (see, e.g., FIG. 13). An additional lead 117 can be used to couple the signal generator 109 to other components of the system 100, which can include a user interface 112 and a controller 110, where it is to be understood that as an alternative to the use of the lead 117, the signal generator 109 can be wirelessly connected to the rest of the system 50. The system can also include an isolated power system 111 and/or a patient monitor system. Further, it should be understood that while the system 100 of FIG. 2 illustrates a configuration where electrical signals can be delivered to target neural tissue, non-neural tissue, or a combination thereof utilizing electrodes 107a and/or 107b coupled to an implantable signal generator 109 via a lead 108, the electrodes 107a and/or 107b can alternatively be coupled to an external signal generator via a wireless antenna system. Regardless, the electrodes 107a and/or 107b can be in the form of an electrode assembly that can deliver electrical signals to a patient to provide therapy to the patient and/or improve one or more of the patient's symptoms based on, for example, the specific location of the electrodes, as discussed in more detail in FIGS. 3-7 below.

Figure 3:
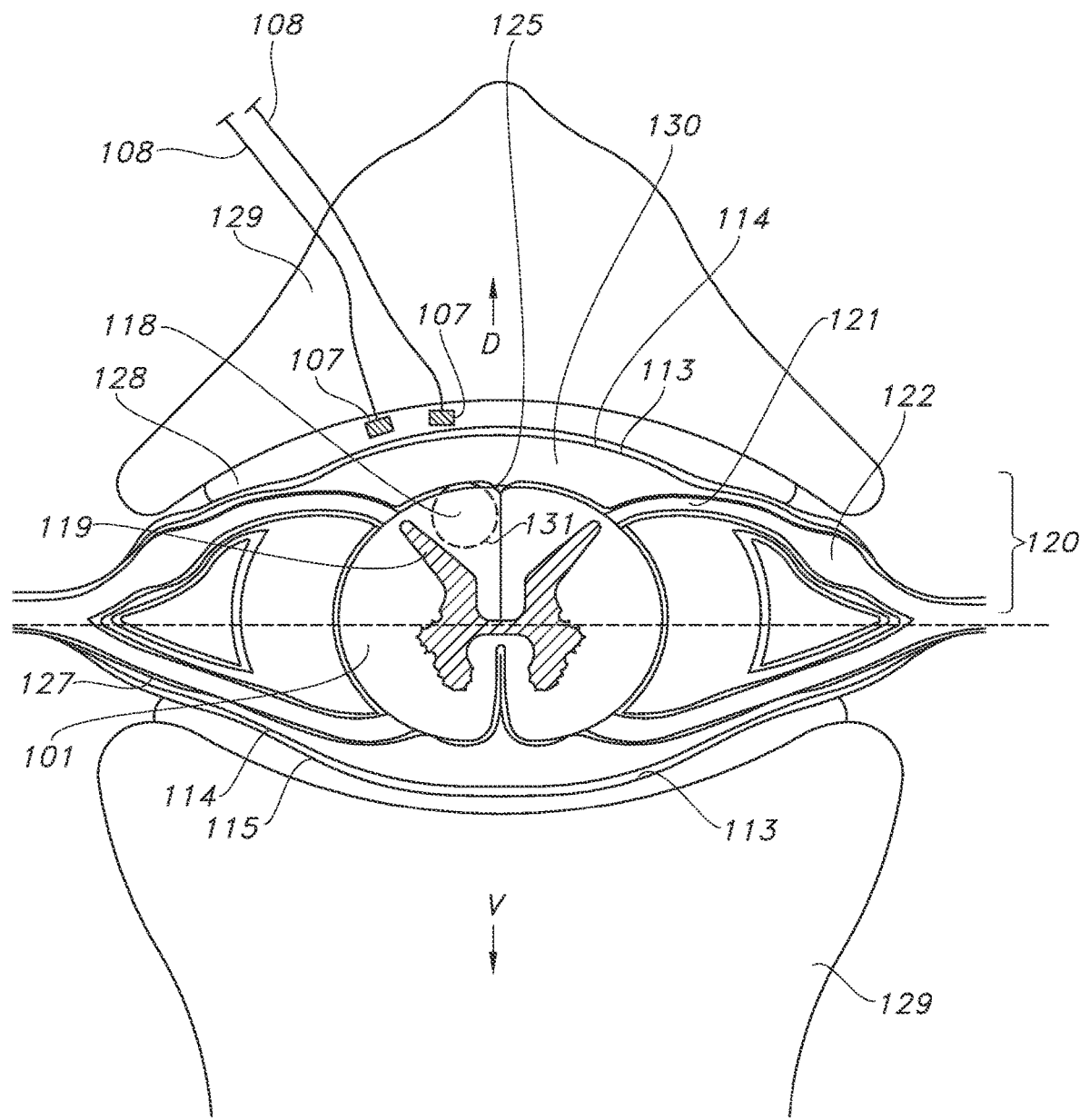
FIG. 3 is a zoomed-in view of the spinal cord and illustrates at least one option for electrode placement according to the system of FIG. 2, where the target tissue is located within or adjacent a dorsal region of the spinal cord, such as the dorsal columns.

Referring now to FIG. 3, the placement of the electrode or electrodes 107 (e.g., electrode array) in order to deliver one or more electrical signals to an area within or adjacent target neural tissue, non-neural tissue, or a combination thereof 131 located adjacent a dorsal region 120 of the spinal cord 101, and in particular a dorsal column 118, is discussed in more detail, where the dorsal D and ventral V directions of the spinal cord 101 are labeled for reference purposes. For instance, one or more electrodes 107 can be positioned within a portion of the epidural space 128 of the patient 116 adjacent a dorsal region 120 of the spinal cord 101, where the dorsal region 120 of the spinal cord 101 can be identified via locating the posterior median sulcus 125. As shown, the epidural space 128 is positioned between the bone 129 (vertebrae) and the dura mater 115. Thus, electrical signals transmitted by the electrode(s) 107 must be configured to pass through the dura mater 115, subdural cavity 113, arachnoid mater 114, subarachnoid cavity 130, and pia mater 127 to reach the target neural tissue, non-neural tissue, or a combination thereof 131 and deliver the desired electrical signals therein. By placing the electrode or electrodes 107 in the epidural space 128 adjacent a dorsal region 120 of the spinal cord 101, electrical signals can be delivered to target neural tissue, non-neural tissue, or a combination thereof 131 located within or adjacent a dorsal column 118 to provide therapy to the patient. It is also to be understood that the electrode or electrodes 107 can be positioned in any suitable location in the dorsal region 120 of the spinal cord 101 in order to deliver electrical signals to an area within or adjacent other target neural tissue, non-neural tissue, or a combination thereof, such as tissue located adjacent a dorsal horn 119 or a dorsal root 121. Specific diseases or conditions that can be treated based on stimulation of the dorsal region of the spinal cord, and in particular, the dorsal columns include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain, and fibromyalgia.

Figure 4:
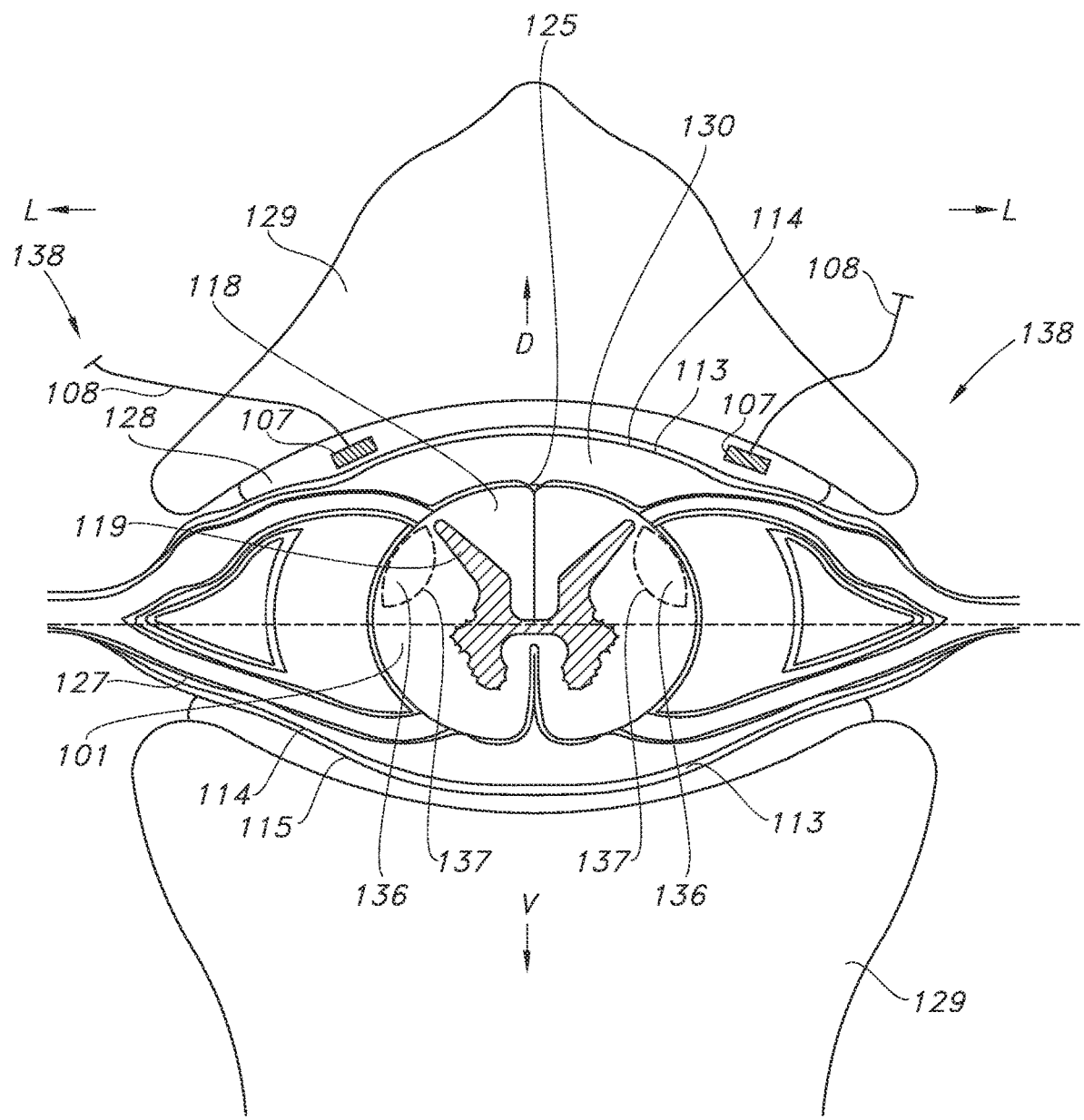
FIG. 4 is a zoomed-in view of the spinal cord and illustrates at least one other option for electrode placement according to the system of FIG. 2, where the target tissue is located within or adjacent to the dorsolateral region of the spinal cord, such as the dorsolateral funiculus.

Referring now to FIG. 4, the placement of the electrode or electrodes 107 (e.g., an electrode array) in order to deliver one or more electrical signals to an area within or adjacent target neural tissue, non-neural tissue, or a combination thereof 137 located in a dorsolateral region 138 of the spinal cord 101 is discussed in more detail, where the dorsal D, ventral V, and lateral L directions are labeled for reference purposes. For instance, one or more electrodes 107 can be positioned adjacent a dorsolateral region 138 of the spinal cord 101. By placing the electrode or electrodes 107 adjacent a dorsolateral region 138 of the spinal cord 101, electrical signals can be delivered to target neural tissue, non-neural tissue, or a combination thereof 137 located within or adjacent a dorsolateral region 138 of the spinal cord 101 to provide therapy to the patient. Specifically, nerve fiber activity in the right or left dorsolateral funiculus 136 or a combination thereof can be altered via electrical signals in order to treat or alleviate symptoms associated various conditions. Specific diseases or conditions that can be treated based on stimulation of the dorsolateral region of the spinal cord, and in particular, the dorsolateral funiculus include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain, and fibromyalgia.

Figure 5:
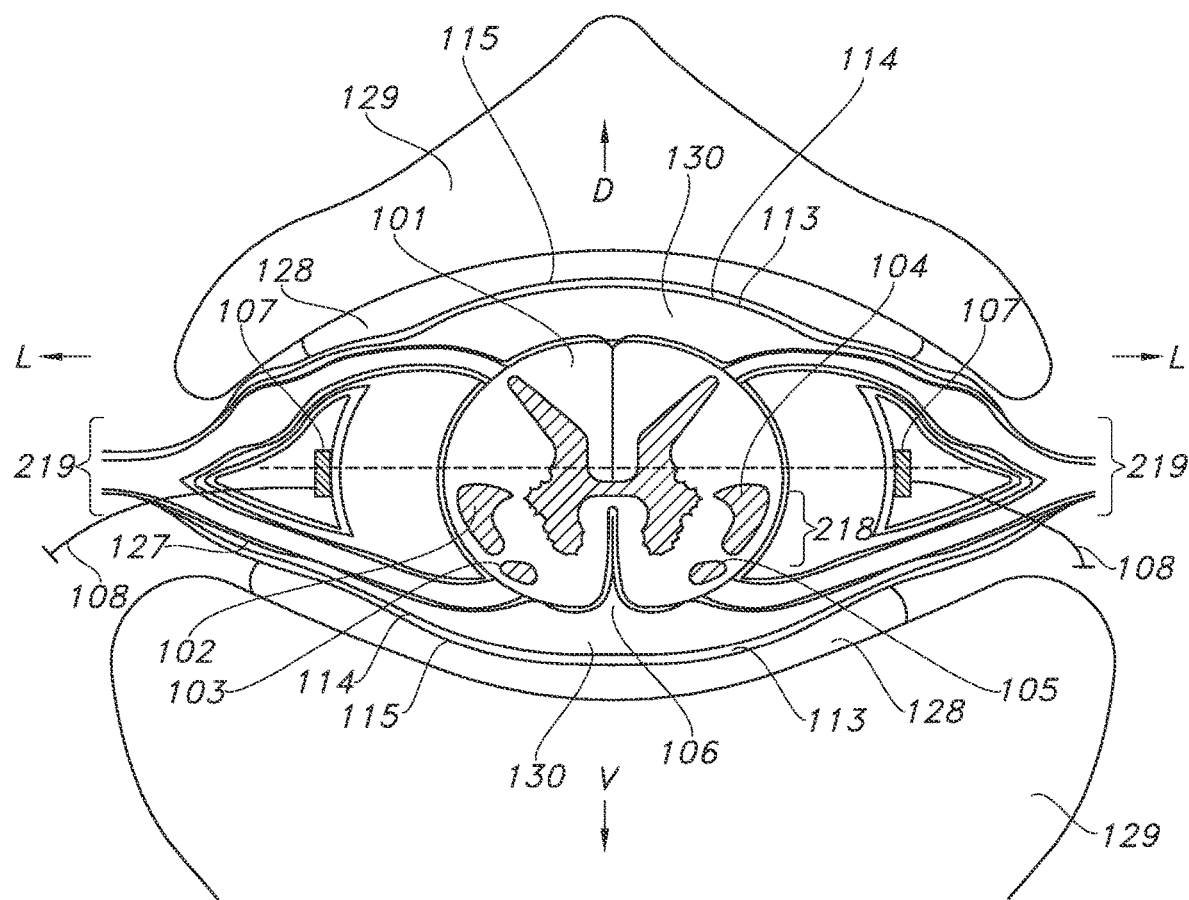
FIG. 5 is a zoomed-in view of the spinal cord and illustrates at least one other option for electrode placement according to the system of FIG. 2, where the target tissue is located within or adjacent the lateral region of the spinal cord, such as the spinothalamic tract.

Referring now to FIG. 5, the placement of the electrode or electrodes 107 (e.g., an electrode array) in order to deliver one or more electrical signals to an area within or adjacent target neural tissue, non-neural tissue, or a combination thereof 218 located in a lateral region 219 of the spinal cord 101 is discussed in more detail, where the dorsal D, ventral V, and lateral L directions are labeled for reference purposes. For instance, one or more electrodes 107 can be positioned adjacent a lateral region 219 of the spinal cord 101. By placing the electrode or electrodes 107 adjacent lateral region 219 of the spinal cord 101, electrical signals can be delivered to target neural tissue, non-neural tissue, or a combination thereof 218 located within or adjacent a lateral region 219 of the spinal cord 101 to provide therapy to the patient. Specifically, nerve fiber activity in the right lateral spinothalamic tract 102, the left lateral spinothalamic tract 104, or a combination thereof can be altered via electrical signals in order to treat or alleviate symptoms associated various conditions. Moreover, it is to be understood that nerve fiber activity in the right anterior spinothalamic tract 103, the left anterior spinothalamic tract 105, or a combination thereof can also be altered via electrical signals based on the specific positioning of the one or more electrodes 107. Specific diseases or conditions that can be treated based on stimulation of the lateral region of the spinal cord, and in particular, the lateral spinothalamic tract include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain, and fibromyalgia.

Figure 6:
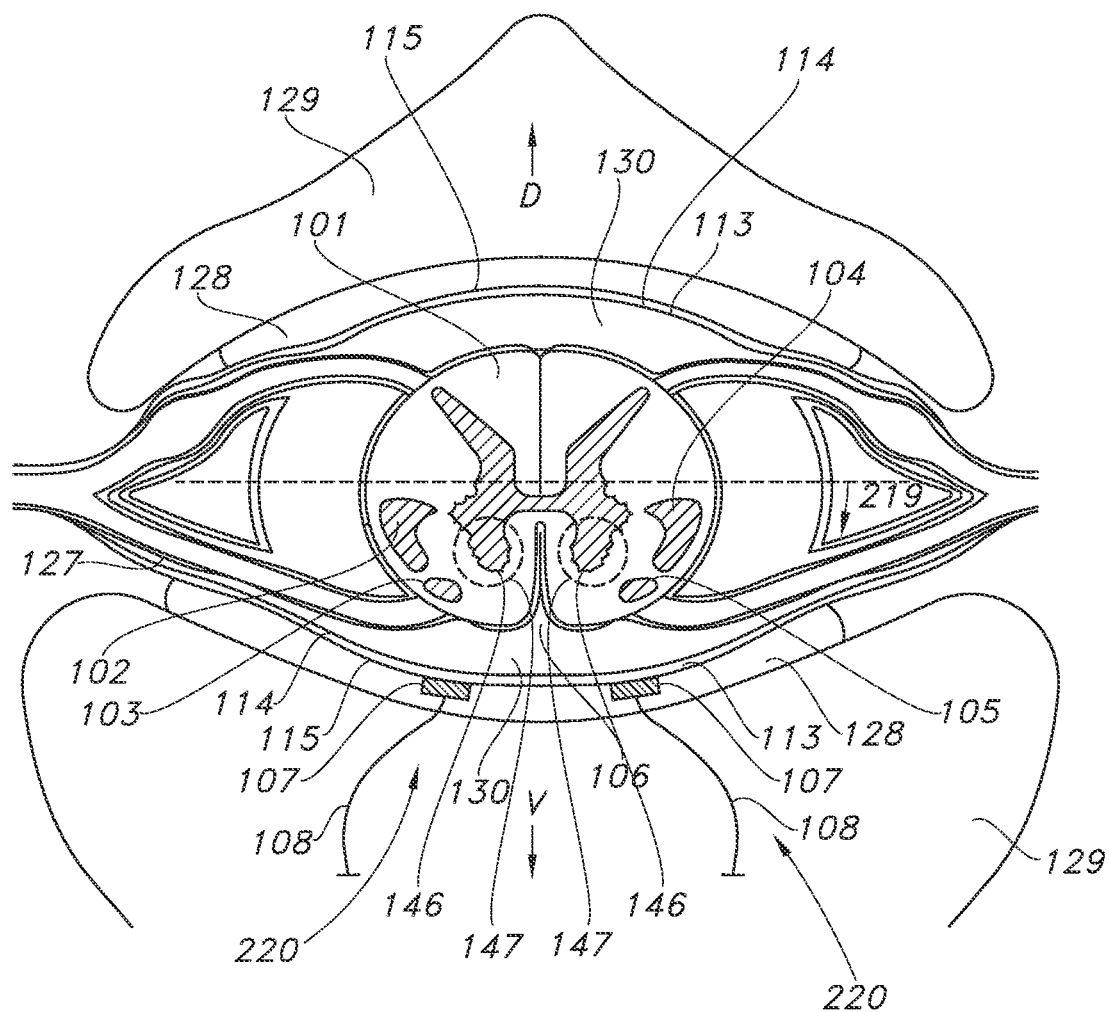
FIG. 6 is a zoomed-in view of the spinal cord and illustrates at least one other option for electrode placement according to the system of FIG. 2, where the target tissue is located with or adjacent the ventral region of the spinal cord, such as the ventral horn.

Referring now to FIG. 6, the placement of the electrode or electrodes 107 (e.g., an electrode array) in order to deliver one or more electrical signals to an area within or adjacent target neural tissue, non-neural tissue, or a combination thereof 147 located in a ventral region 220 of the spinal cord 101 is discussed in more detail, where the dorsal D and ventral V directions are labeled for reference purposes. For instance, one or more electrodes 107 can be positioned within a portion of the epidural space 128 of the patient 116 adjacent a ventral region 220 of the spinal cord 101, where the ventral region 220 of the spinal cord 101 can be identified via locating the anterior median fissure 106. As shown, the epidural space 128 is positioned between the bone 129 (vertebrae) and the dura mater 115. Thus, electrical signals transmitted by the electrode(s) 107 are configured to pass through the dura mater 115, subdural cavity 113, arachnoid mater 114, subarachnoid cavity 130, and pia mater 127 to reach the target neural tissue, non-neural tissue, or a combination thereof 147 and deliver the desired electrical signals therein. By placing the electrode or electrodes 107 in the epidural space 128 adjacent a ventral region 220 of the spinal cord 101, electrical signals can be delivered to target neural tissue, non-neural tissue, or a combination thereof 147 located in a ventral region 220 of the spinal cord 101 to provide therapy to the patient. Specifically, in one particular embodiment, nerve fiber activity in the right or left ventral horn 146 or a combination thereof can be altered via electrical signals in order to treat or alleviate symptoms associated various conditions. Specific diseases or conditions that can be treated based on stimulation of the ventral region of the spinal cord include, for example, motoneuron disease (amyotrophic lateral sclerosis; progressive muscular atrophy; progressive bulbar palsy; primary lateral sclerosis; hereditary spastic paraplegia), spinal muscular atrophy (infantile and juvenile spinal muscular atrophy; focal amyotrophy), and multiple sclerosis.

Figure 7:
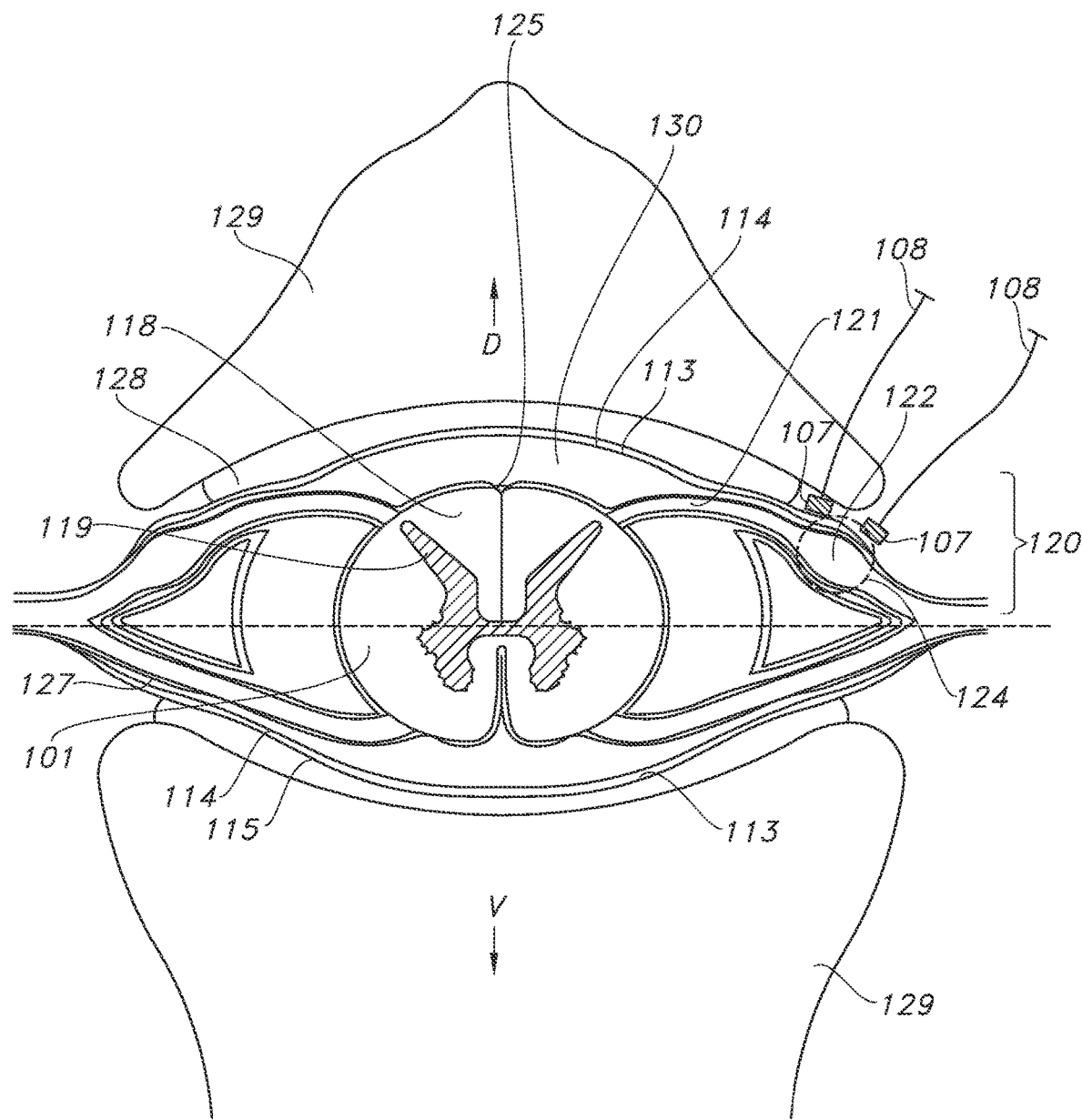
FIG. 7 is a zoomed-in view of the spinal cord and illustrates at least one other option for electrode placement according to the system of FIG. 2, where the target tissue is located within or adjacent a dorsal root ganglion.

Referring now to FIG. 7, the placement of the electrode or electrodes 107 (e.g., an electrode array) in order to deliver one or more electrical signals to an area within or adjacent target neural tissue, non-neural tissue, or a combination thereof 124 located adjacent or near a dorsal region 120 of the spinal cord 101, and in particular a dorsal root ganglion 122, is discussed in more detail, where the dorsal D and ventral V directions of the spinal cord 101 are labeled for reference purposes. For instance, one or more electrodes 107 can be positioned within a portion of the epidural space 128 of the patient 116 adjacent a dorsal (or posterior) portion 120 of the spinal cord 101, where the dorsal (or posterior) portion 120 of the spinal cord 101 can be identified via locating the posterior median sulcus 125. As shown, the epidural space 128 is positioned between the bone 129 (vertebrae) and the dura mater 115. Thus, electrical signals transmitted by the electrode(s) 107 are configured to pass through the dura mater 115, subdural cavity 113, arachnoid mater 114, subarachnoid cavity 130, and pia mater 127 to reach the target neural tissue, non-neural tissue, or a combination thereof 124 and deliver the desired electrical signals therein. By placing the electrode or electrodes 107 in the epidural space 128 adjacent a dorsal D (or posterior) portion 120 of the spinal cord 101, electrical signals can be delivered to target neural tissue, non-neural tissue, or a combination thereof 124 located within or adjacent a dorsal root ganglion 122 to provide therapy to the patient. Specific diseases or conditions that can be treated based on stimulation of the dorsal root ganglion include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain and fibromyalgia.

Figure 8:
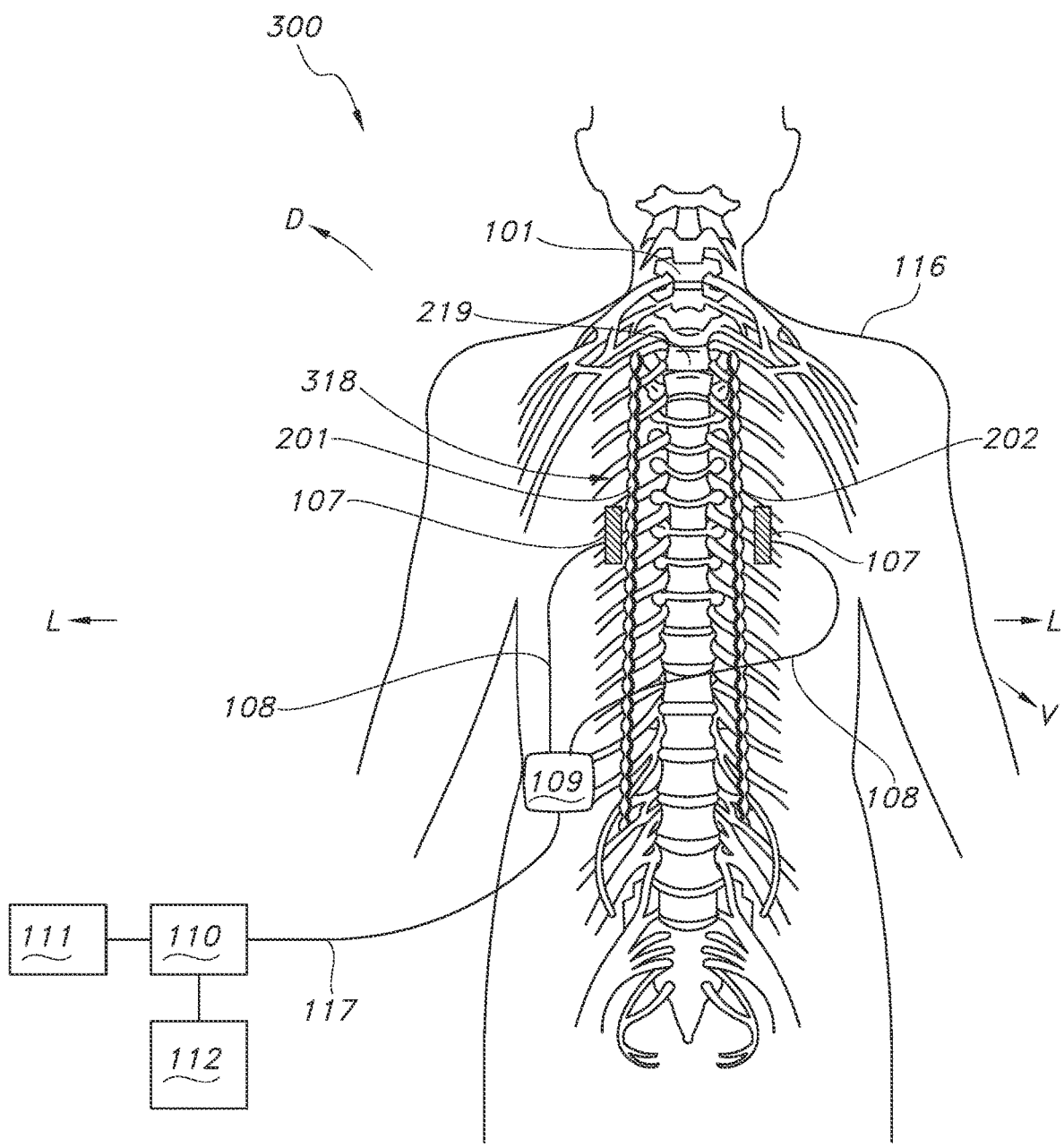
FIG. 8 illustrates at least one embodiment of a system for delivering one or more electrical signals to target neural tissue, non-neural tissue, or a combination thereof in a patient, where the target tissue is located within or adjacent a sympathetic chain ganglion.

Referring now to FIG. 8, there is illustrated a system 300 for delivering one or more electrical signals to provide therapy to a patient 116, where the target neural tissue, non-neural tissue, or a combination thereof 318 located adjacent a ventral or anterior region 219 of a spinal cord 101 of the patient 116. It should be appreciated that the system 300 of FIG. 8 may include similar elements and/or features to the system 50 described in reference to FIG. 1. In particular, the target neural tissue, non-neural tissue, or a combination thereof 318 can be a sympathetic chain ganglion located in the right sympathetic chain 201, the left sympathetic chain 202, or a combination thereof. As shown in FIG. 8, in some embodiments, the system 300 can include multiple devices to control and deliver electrical signals to an area within or adjacent target neural tissue, non-neural tissue, or a combination thereof 318 located adjacent a ventral V (or anterior) region 219 of the spinal cord 101 to provide therapy to the patient 116. In general, the system 300 of FIG. 8 can include one or more electrodes 107 that are connected by an electrical lead 108 to a signal generator 109. As described herein, multiple electrodes 107 may be arranged into an electrode array in some embodiments (see, e.g., FIG. 13). An additional lead 117 can be used to couple the signal generator 109 to the rest of the system 300, which can include a user interface 112, and a controller 110, where it is to be understood that as an alternative to the use of the lead 117, the signal generator 109 can be wirelessly connected to the rest of the system 50. The system may also include an isolated power system 111 and/or a patient monitor system. Further, it should be understood that while the system 300 of FIG. 8 illustrates a configuration where electrical signals can be delivered to target neural tissue, non-neural tissue, or a combination thereof utilizing an electrode or electrodes 107 coupled to an implantable signal generator 109 via a lead 108, the electrode or electrodes 107 can alternatively be coupled to an external signal generator via a wireless antenna system. Regardless, the electrode or electrodes 107 can be in the form of an electrode assembly that can that can deliver electrical signals to a patient to provide therapy to the patient and/or improve one or more of the patient's symptoms.

Figure 9:
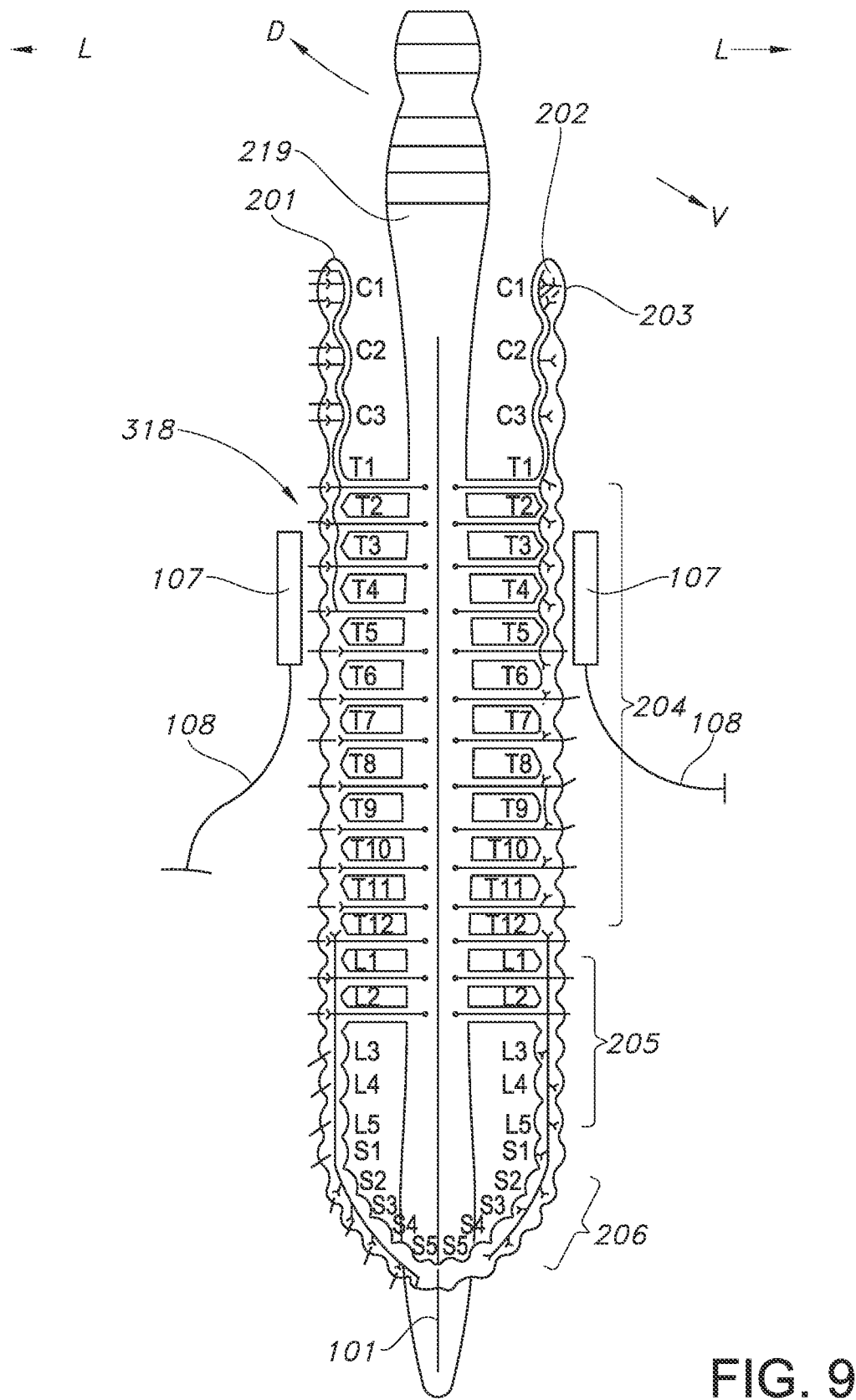
FIG. 9 is a zoomed-in view of the sympathetic chain and illustrates at least one option for electrode placement according to the system of FIG. 8.

Referring now to FIG. 9, the placement of the electrode or electrodes 107 (e.g., an electrode array) is discussed in more detail. For instance, one or more electrodes 107 can be positioned adjacent a region of the right sympathetic chain 201 or the left sympathetic chain 202 of the patient 116, where the sympathetic chains 201 and 202 are located ventral and lateral to a ventral (or anterior) region 219 of the spinal cord 101. By placing the electrode or electrodes 107 adjacent target neural tissue, non-neural tissue, or a combination thereof 318 located lateral and ventral to a ventral (or anterior) region 219 of the spinal cord 101, one or more electrical signals can be delivered to the target neural tissue, non-neural tissue, or a combination thereof 318 (e.g., a ganglion or ganglia of the right sympathetic chain 201 or the left sympathetic chain 202) to provide therapy to the patient.

For instance, electrical signals can be delivered to a ganglion or ganglia associated with the cervical portion 203, the thoracic portion 204, the lumbar portion 205, or the sacral portion 206 of the right sympathetic chain 201 or the left sympathetic chain 202, or any combination thereof to provide therapy to the targeted area or areas. In one particular embodiment, one or more electrodes 107 (e.g., an electrode array) can be placed adjacent the cervical region 203 of the sympathetic chain to affect nerve fiber activity associated with levels C1-C3, which can affect nerve fiber activity associated with the eyes, the lachrymal glands, the salivary glands, and the sweat glands, hair follicles, and blood vessels of the head, neck, and arms. In another embodiment, one or more electrodes 107 (e.g., an electrode array) can be placed adjacent levels T1-T4 of the thoracic region 204, which can affect nerve fiber activity associated with the heart and lungs. In an additional embodiment, one or more electrodes 107 (e.g., an electrode array) can be placed adjacent levels T5-T9 of the thoracic region 204, which can affect nerve fiber activity associated with the stomach, duodenum, pancreas, liver, kidneys, and adrenal medulla. In yet another embodiment, one or more electrodes 107 (e.g., an electrode array) can be placed adjacent levels T10-T11 of the thoracic region 204, which can affect nerve fiber activity associated with the stomach and duodenum. In one more embodiment, one or more electrodes 107 (e.g., an electrode array) can be placed adjacent level T12 of the thoracic region 204 and levels L1-L3 of the lumbar region 205, which can affect nerve fiber activity in the colon, rectum, bladder, and external genitalia. In still another embodiment, one or more electrodes 107 (e.g., an electrode array) can be placed adjacent levels L4-L5 of the lumbar region 205 and levels S1-S3 of the sacral region 206, which can affect nerve fiber activity associated with the sweat glands, hair follicles, and blood vessels of the lower limbs. In another embodiment, one or more electrodes 107 (e.g., an electrode array) can be placed adjacent levels S4-S5 of the sacral region 206, which can affect nerve fiber activity associated with the sweat glands, hair follicles, and blood vessels of the perineum. Specific diseases or conditions that can be treated based on stimulation of a sympathetic nervous system include, for example, complex regional pain syndrome, peripheral vascular disease and chronic limb ischemia, angina pain, diabetic pain, abdominal/visceral pain syndrome, phantom limb pain, Raynaud's syndrome, diabetic peripheral neuropathy, hypertension, hypotension, headache and migraine, and inflammatory pain such as arthritis, irritable bowel pain, osteoarthritis pain, and fibromyalgia. It should be appreciated that, in some embodiments, the electrode(s) 107 may be placed beside other autonomic structures including parasympathetic nerves (e.g., vagus nerve).

Figure 10:
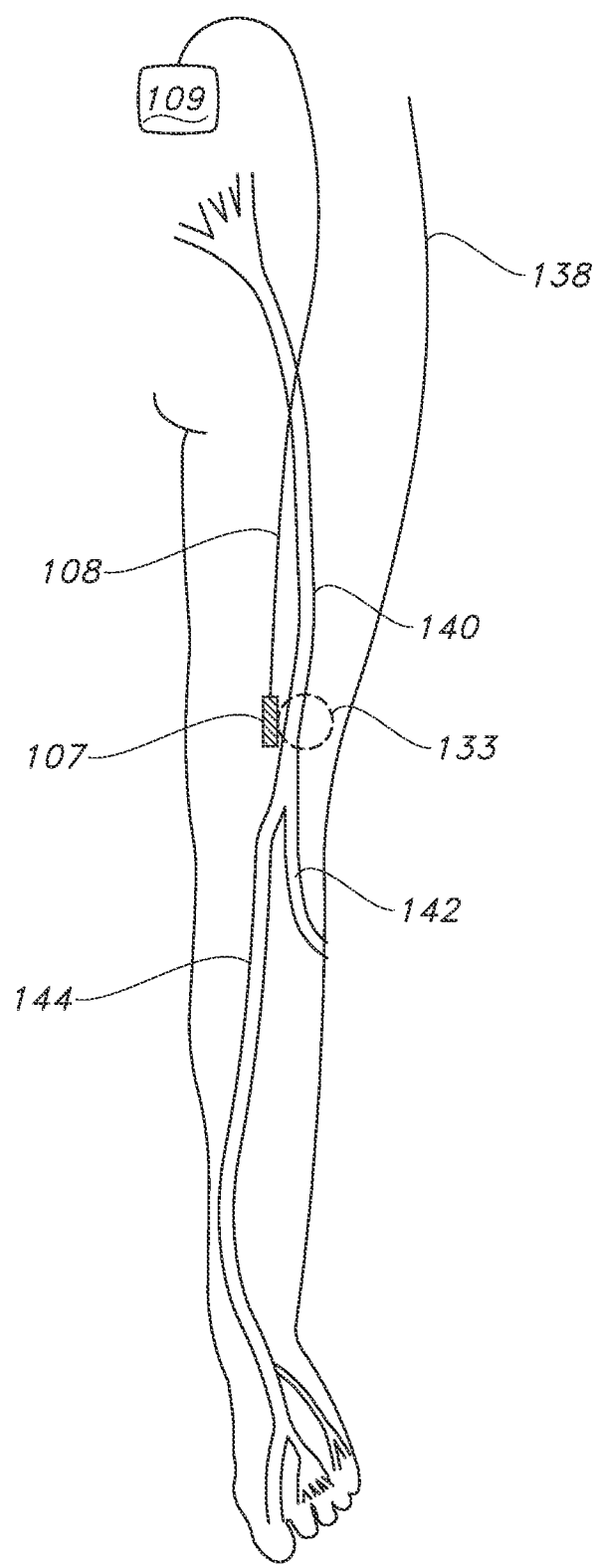
FIG. 10 illustrates at least one embodiment of a system for delivering one or more electrical signals to target neural tissue, non-neural tissue, or a combination thereof in a patient, where the target tissue is located within or adjacent a peripheral nerve.

Referring now to FIG. 10, the placement of the electrode or electrodes 107 (e.g., an electrode array) in order to deliver one or more electrical signals to an area within or adjacent target neural tissue, non-neural tissue, or a combination thereof 133 located adjacent or near a peripheral nerve is discussed in more detail. For instance, one or more electrodes 107 can be positioned near or adjacent a peripheral nerve at any location along its length, where the peripheral nerve can run, for instance, down the length of the leg 138 of the patient 116. In the particular embodiment of FIG. 10, the target tissue 133 is located adjacent the sciatic nerve 140, although it is to be understood that neural tissue, non-neural tissue, or a combination thereof can be located adjacent any peripheral nerve in the leg (e.g., the common peroneal nerve 142, the tibial nerve 144, etc.), or any other location in the body. By placing the electrode or electrodes 107 adjacent or near a peripheral nerve, electrical signals can be delivered to the target neural tissue, non-neural tissue, or a combination thereof 133 to provide therapy to the patient. Specific diseases or conditions that can be treated based on stimulation of a peripheral nerve include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, headache and migraine, cervical neuritis, post-herpetic neuralgia, vertigo, tinnitus, hearing loss and inflammatory pain such as arthritis, irritable bowel pain, overactive bladder, bowel incontinence or constipation, osteoarthritis pain, and fibromyalgia. For example, electrical signals can be used to stimulate the sacral nerve roots to treat overactive bladder, fecal incontinence, and/or sexual dysfunction. In some embodiments, the electrode(s) may be placed adjacent or near a cranial nerve.

It should be appreciated from the description that the electrode(s) 107 may be placed in particular location in order to treat a particular condition using the electrical stimulation technologies described herein. For example, in an embodiment, the electrode(s) 107 may be placed within an epidural space between T7 and T12 of a thoracic portion of the patient's spine to treat the patient for spinal lumbar pain. In another embodiment, the electrode(s) 107 may be placed within an epidural space between C2 and T1 of a cervical portion of the patient's spine to treat the patient for spinal cervical pain. In another embodiment, the electrode(s) 107 may be placed within an epidural space between C2 and T8 of the patient's spine to treat angina pain. In another embodiment, the electrode(s) 107 may be placed within an epidural space between C2 and T8 of the patient's spine to treat abdominal pain. In another embodiment, the electrode(s) 107 may be placed within an epidural space between T10 and L5 of the patient's spine to treat peripheral vascular disease. In another embodiment, the electrode(s) 107 may be placed within an epidural space between T7 and T12 in the thoracic spine to treat spinal lumbar pain disorders. In another embodiment, the electrode(s) 107 may be placed within an epidural space between C2 and T1 of a cervical portion of the patient's spine to treat the patient for upper limb ischemia. In another embodiment, the electrode(s) 107 may be placed at or within a dorsal root ganglion of the patient's spin to treat chronic or acute pain. In another embodiment, the electrode(s) 107 may be placed within a sacral portion of the patient's spine to treat urinary or fecal incontinence. In various embodiments, the electrode(s) 107 may be placed near or around the lumbar sympathetic plexus, the celiac sympathetic plexus, the hypogastric sympathetic plexus, or the stellate ganglion to treat chronic or acute pain of the limb, abdomen, pelvic area, or upper extremity, respectively. In another embodiment, the electrode(s) 107 may be placed near or around the patient's brain to treat movement disorders, Parkinson's, pain, psychiatric and/or seizure disorders. In another embodiment, the electrode(s) 107 may be placed near or around the patient's vagus nerve to treat seizure disorders, obesity, pain, or autonomic disorders. In another embodiment, the electrode(s) 107 may be placed near or around a peripheral nerve of the patient to treat acute pain, chronic pain, fecal or urinary incontinence, seizure disorders, movement disorders, obesity, spasticity, and to modulate other unpleasant neurological conditions. In another embodiment, the electrode(s) 107 may be placed near or around the patient's somatic tissue, muscles, connective tissue, or non-neural tissue to treat acute pain, chronic pain, fecal or urinary incontinence, seizure disorders, movement disorders, obesity, spasticity, and to modulate other unpleasant neurological conditions. In another embodiment, the electrode(s) 107 may be placed near or around the patient's visceral tissue or organs, and non-neural tissue to treat acute pain, chronic pain, fecal or urinary incontinence, seizure disorders, movement disorders, obesity, spasticity, and to modulate other unpleasant neurological conditions. In some embodiments, the electrode array may be positioned such that a distal electrical contact of the electrode array stimulates the patient's thoracic spine at T8 and a proximal electrical contact of the electrode array stimulates the patient's vertebral body at T10 to treat the patient for intractable leg and back pain.

The various components of the systems 50, 100, and 300 described in FIGS. 1-10 may form the portion of an electrical stimulation system 400 as described below in more detail in reference to FIG. 11.

Figure 11:
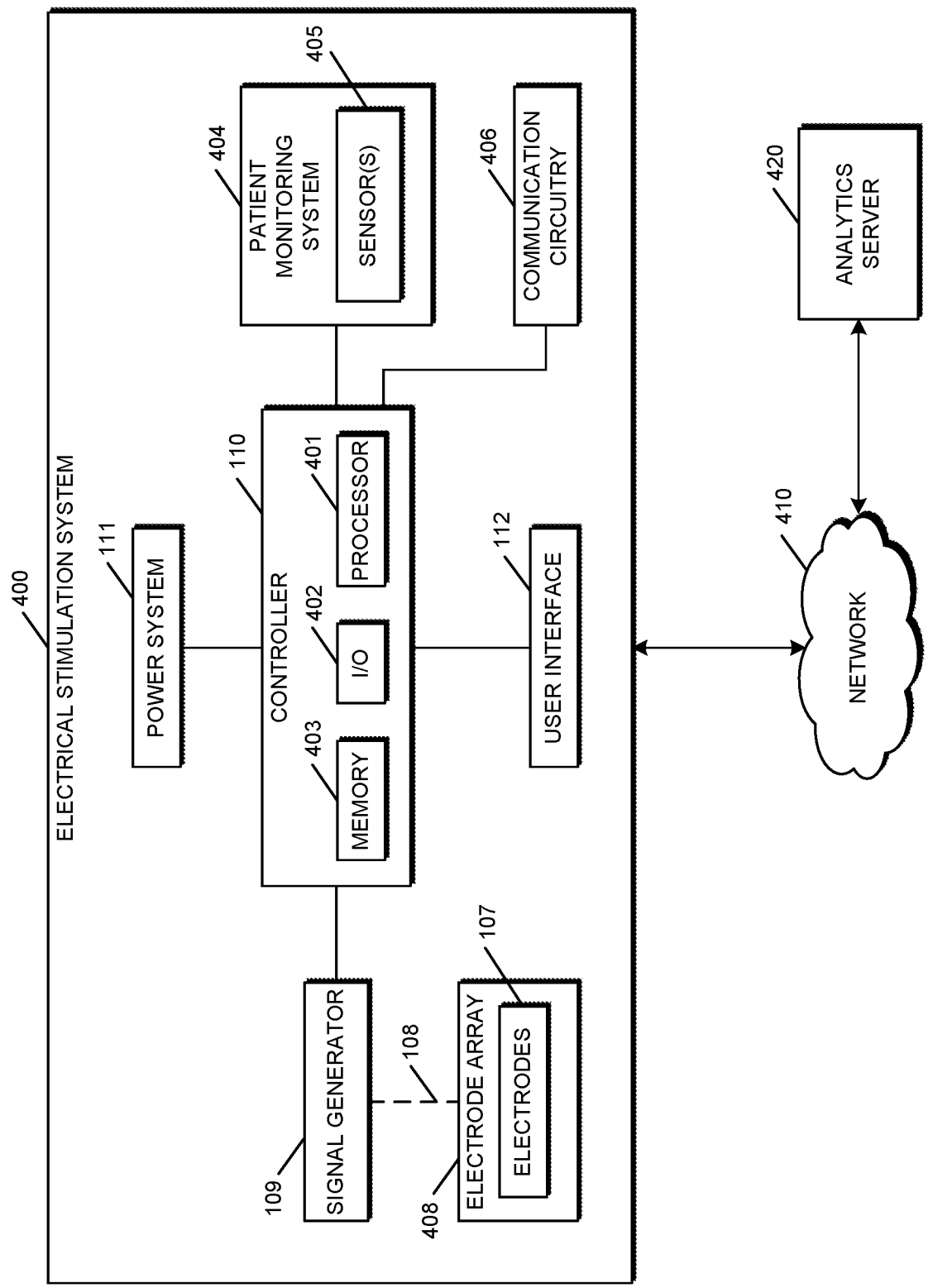
FIG. 11 is a simplified block diagram of at least one embodiment of an electrical stimulation system for providing therapy to a patient via the application of one or more electrical signals.

Referring now to FIG. 11, a simplified block diagram of at least one embodiment of an electrical stimulation system 400 for providing therapy to a patient via the application of one or more electrical signals and otherwise performing the functions described herein is shown. The illustrative electrical stimulation system 400 includes a plurality of electrodes 107, a signal generator 109, a controller 110, a power system 111, a user interface 112, a patient monitoring system 404, and a communication circuitry 406. Further, in the illustrative embodiment, the controller 110 includes a processor 401, an input/output ("I/O") subsystem 402, and a memory 403, and the patient monitoring system 404 includes one or more sensors 405. Additionally, as described herein, the electrodes 107 may collectively form one or more electrode arrays 408. It should be appreciated that one or more of the components of the electrical stimulation system 400 described herein may be embodied as, or form a portion of, one or more embedded controllers and/or integrated circuits. For example, in some embodiments, the processor 401, the I/O subsystem 402, the memory 403 and/or other components of the electrical stimulation system 400 may be embodied as, or form a portion of, a microcontroller or SoC (e.g., such as an embodiment in which the controller 110 is a microcontroller). Further, depending on the particular embodiment, the components of the electrical stimulation system 400 may be closely positioned to one another or spatially distributed (i.e., separated from one another) depending on the particular embodiment. Additionally, although only a single generator 109, controller 110, power system 111, user interface 112, patient monitoring system 404, communication circuitry 406, electrode array 408, processor 401, I/O subsystem 402, and memory 403 are illustratively shown in FIG. 11, it should be appreciated that a particular electrical stimulation system 400 may include multiple signal generators 109, controllers 110, power systems 111, user interfaces 112, patient monitoring systems 404, communication circuitries 406, electrode arrays 408, processors 401, I/O subsystems 402, and/or memories 403 in various embodiments. As described herein, it should be appreciated that the randomization of the stimulation can be managed by hardware, firmware, and/or software depending on the particular embodiment.

The electrodes 107 of the electrode array 408 can be used to deliver the electrical signals to the target neural tissue, non-neural tissue, or a combination thereof as described herein. Depending on the particular embodiment, the electrode array 408 can be implantable, percutaneous, or transcutaneous. Further, as described herein, the shape, size, material composition, inter-electrode spacing, and/or other parameters of the electrodes 107 or electrode array 408 can be specific to contouring the electrical field surrounding the target neural tissue, non-neural tissue, or a combination thereof, to enable specific therapy to be provided to the target neural tissue, non-neural tissue, or a combination thereof. It should be appreciated that the electrodes 107 of the electrode array 408 may be embodied on or electrically coupled to one or more electrical leads 108, which may be connected to the signal generator 109 as described herein. An exemplary embodiment of the electrode array 408 is described in greater detail below in reference to FIG. 13. It should be appreciated that the electrode array 408, the signal generator 109, and/or the controller 110 include electrical circuitry that allow for the real-time selection of specific electrodes 107 of the electrode array 408 as being anodes, cathodes, or unused/off during the transmission of an electrical stimulation signal.

As shown in the figures, the electrodes 107 (or electrode array 408) may be connected to an implantable signal generator 109 through an electrical lead 108. Alternatively, in some embodiments, the signal generator 109 can be external and can be wirelessly connected to the electrodes 107 (or electrode array 408). In some embodiments, the signal generator 109 can be configured to generate and deliver electrical signals to provide therapy to a patient that can be customized based on patient feedback. As described herein, in the illustrative embodiment, the patient feedback may be based on self-report (e.g., introspection, observations of unwanted sensory—and/or motor activity, autonomic dysfunction, etc.) via a graphical user interface (see, for example, FIG. 17). However, in some embodiments, it should be appreciated that patient feedback may, additionally or alternatively, be determined from data generated by sensors measuring physiological outcomes, based on data from artificial intelligence or machine learning systems (e.g., output or feedback data), or based on combinations thereof.

The use of multiple signal generators 109 (or multiple waveform generators) may enhance the resolution of the signal generator 109 by independently powering some electrical contacts with one signal, and powering other contacts with a different signal, and/or by allowing one waveform to be added to another waveform and delivered through the same set of contacts. Accordingly, an electrical stimulation system 400 that contains multiple independent signal generators 109 (or multiple waveform generators) may enable improved control of electrical contacts, may enable improved control of the waveform's randomness, and/or may facilitate interactions between frequency bands (e.g., multi-waveform, physiological, and psychophysical masking).

Regardless of the particular type or combination of electrical signals utilized, the electrical signals can be adjusted, such that the energy contained within a particular frequency band, and for all frequency bands of energy delivered to the tissue, can be adjusted to best treat the patient as described herein. In some embodiments, the adjustable electrical energy can be adjusted to deliver electrical signals with intensities ranging from about 1 mA (or 0.1 mA) to about 100 mA and from about 1 V (or 0.1 V) to about 200 V (peak-to-peak) for each frequency band included in the spectrum. In some embodiments, the spectrum of electrical signals includes frequencies ranging from about 0 Hz to about 100 kHz (or about 0 Hz to about 500 kHz), and is composed of adjustable frequency bands. It should be appreciated that the size of the frequency bands may vary depending on the particular embodiment (e.g., 10 Hz bands, 100 Hz bands, 1000 Hz bands, etc.). In some embodiments, the spectrum of electrical signals includes frequencies ranging from about 0 Hz to about 25 kHz (or about 0 Hz to about 25 kHz), and each of the frequency bands within the frequency range may have a bandwidth of 1 kHz or 2 kHz. In another embodiment, the electrical stimulation signal may have a frequency range of about 0.05 Hz to about 2 kHz, and/or each of the frequency bands within the frequency range may have a bandwidth of about 150 Hz. Although various frequency ranges are described herein as being nominally zero or "from about 0 Hz," it should be appreciated that such lower bound may be some non-zero frequency greater than 0 Hz in some embodiments (e.g., 1 Hz). Moreover, the frequency band that receives power can be determined in a random fashion.

The power supply, power source, or power system 111 is configured to supply power to the controller 110 and/or other components of the electrical stimulation system 400. In some embodiments, the power system 111 is an independent, untethered, and portable power source configured to supply power to the electrical stimulation system 400 to perform the various functions described herein. For example, the power system 111 may include one or more batteries, battery packs, capacitors, super capacitors, solar cells, and/or other power supplies. Depending on the particular embodiment, the power system 111 may or may not be rechargeable. In other embodiments, the power system 111 may be line powered via AC mains and/or another suitable power source. It should be appreciated that the power system 111 can include both external and internal portions, where the internal portion of the power system can include a battery, such as a lithium battery, and the external portion of the power system 111 can be plugged into a wall and used to recharge the battery as needed. In such embodiments, the external portion of the power system 111 can transmit power to the signal generator 109 as directed by the controller 110 via RF signals/electromagnetic induction, or power can be transmitted to the signal generator 109 via the battery in the internal portion of the power system 111. Further, the external portion of the power system 111 can be used to recharge the battery in the internal portion of the power system 111.

The user interface 112 may be embodied as any one or more devices or components that allow a user to interact with the electrical stimulation system 400. For example, in some embodiments, the user interface 112 can be in the form of a computer that interacts with the controller 110 and is powered by a power system 111. In particular, in some embodiments, the computer can operate software designed to record signals passed from the controller 110, and to drive the controller's output. Possible software packages include Cambridge Electronic Design's (UK) SPIKE program. The software can be programmable and can record and analyze electrophysiological signals, as well as direct the controller 110 to deliver the electrical signals described herein. Further, in some embodiments, the user interface 112 may include one or more peripheral devices such as, for example, a keyboard, mouse, display, status indicator, diagnostic tool, speaker, microphone, and/or one or more other suitable peripheral devices.

In some embodiments, the electrical stimulation system 400 may include a patient monitoring system 404. In such embodiments, the patient monitoring system 404 can acquire, amplify/attenuate, and filter physiological signals and then output them to the controller 110. It should be appreciated that the patient monitoring system 404 may include one or more sensors 405. The sensors 405 are configured to generate sensor data (e.g., by virtue of one or more signals), which may be interpreted by the controller 110 (e.g., the processor 401) to determine one or more characteristics associated with the patient and/or the electrical stimulation system 400. By way of example, the sensors 405 may detect various characteristics of the physical environment of the electrical stimulation system 400 (internal and/or external) and/or other suitable characteristics. In various embodiments, the sensors 405 may be embodied as, or otherwise include, environmental sensors, inertial sensors, proximity sensors, optical sensors, electromagnetic sensors, audio sensors, pressure sensors, flow meters, temperature sensors, thermistors, chemical sensors, biopotential electrodes, motion sensors, piezoelectric sensors, cameras, and/or other types of sensors. Of course, the electrical stimulation system 400 may also include components and/or devices configured to facilitate the use of the sensors 405. For example, in some embodiments, the patient monitoring system 404 may include a heart-rate monitor to collect electrocardiogram signals and/or a muscle activity monitor to collect electromyography signals. The heart-rate monitor can include ECG electrodes coupled with an alternating current (AC) amplifier, and the muscle activity monitor can include EMG electrodes coupled with an AC amplifier. Other types of transducers may also be used in other embodiments. As described, physiological signals obtained with the patient monitoring system 404 may be passed through an AC signal amplifier/conditioner. One possible amplifier/conditioner is a Model LP511 AC amplifier available from Grass Technologies, a subsidiary of Astro-Med, Inc., West Warwick, Rhode Island, USA.

The communication circuitry 406 may be embodied as any communication circuitry, transceiver, device, or collection thereof, capable of enabling communications between the electrical stimulation system 400 and other remote devices. The communication circuitry 406 may be configured to use any one or more wired and/or wireless communication technologies and associated protocols. For example, in some embodiments, the illustrative electrical stimulation system 400 may be configured to communicate via Wi-Fi (e.g., infrastructure or ad hoc mode), Wi-Fi Direct, Bluetooth (including Bluetooth Low Energy (BLE)), Zig-Bee, Z-wave, Near Field Communication (NFC), IEEE 802.15, HL7, and/or other suitable wireless communication protocol(s). Further, in some embodiments, the electrical stimulation system 400 may be configured to communicate via Ethernet, Power over Ethernet (PoE), serial communication links, power line communication, and/or another suitable wired communication mechanism.

The controller 110 may be embodied as any type of controller or control system capable of performing the functions described herein. In the illustrative embodiment, the controller 110 can record electrical signal data as well as digital information from the patient monitoring system 404, and can generate electrical signal and digital outputs simultaneously for real-time control of the signal generator 109 based on feedback received from the patient after transmission of the electrical stimulation signals. The controller 110 may have onboard memory to facilitate high-speed data capture, independent waveform sample rates, and on-line analysis. An exemplary controller 110 may be a POWER 1401 data-acquisition interface unit available from Cambridge Electronic Design (UK).

As shown, in some embodiments, the controller 110 includes a processor 401, an I/O subsystem 402, and memory 403.

The processor 401 may be embodied as any type of processor(s) capable of performing the functions described herein. In particular, the processor 401 may be embodied as one or more single or multi-core processors, microcontrollers, or other processor or processing/controlling circuits. For example, in some embodiments, the processor 401 may include or be embodied as an arithmetic logic unit (ALU), central processing unit (CPU), digital signal processor (DSP), and/or another suitable processor(s). The processor 401 may be a programmable type, a dedicated hardwired state machine, or a combination thereof. One or more processors 401 with multiple processing units may utilize distributed, pipelined, and/or parallel processing in various embodiments. Further, the processor 401 may be dedicated to performance of just the operations described herein, or may be utilized in one or more additional applications. In the illustrative embodiment, the processor 401 is of a programmable variety that executes algorithms and/or processes data in accordance with operating logic as defined by programming instructions (such as software or firmware) stored in the memory 403. Additionally or alternatively, the operating logic for the processor 401 may be at least partially defined by hardwired logic or other hardware. Further, the processor 401 may include one or more components of any type suitable to process the signals received from input/output devices or from other components or devices and to provide desired output signals. Such components may include digital circuitry, analog circuitry, or a combination thereof.

The memory 403 may be of one or more types of non-transitory computer-readable media, such as a solid-state memory, electromagnetic memory, optical memory, or a combination thereof. Furthermore, the memory 403 may be volatile and/or nonvolatile and, in some embodiments, some or all of the memory 403 may be of a portable variety, such as a disk, tape, memory stick, cartridge, and/or other suitable portable memory. In operation, the memory 403 may store various data and software used during operation of the electrical stimulation system 400 such as operating systems (e.g., real-time operating systems (RTOS)), applications, programs, libraries, and drivers. The memory 403 is communicatively coupled to the processor 401 via the I/O subsystem 402, which may be embodied as circuitry and/or components to facilitate input/output operations with the processor 401, the memory 403, and other components of the electrical stimulation system 400. For example, the I/O subsystem 402 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. Depending on the particular embodiment, the memory 403 may be included with the processor 401 and/or coupled to the processor 401 depending on the particular embodiment. For example, in some embodiments, the processor 401, the I/O subsystem 402, the memory 403, and/or other components of the electrical stimulation system 400 may form a portion of a system-on-a-chip (SoC) and be incorporated on a single integrated circuit chip.

As shown in FIG. 11, in some embodiments, the electrical stimulation system 400 or a portion thereof (e.g., the controller 110) may be configured to communicate with an analytics server 420 and/or other remote computing device via a network 410. For example, in some embodiments, the electrical stimulation system 400 may transmit patient data (e.g., including an optimal electrical stimulation signature), sensor data, and/or other data to the analytics server 420 for leveraging artificial intelligence, machine learning, and/or other technologies for pattern identification and/or decision-making.

The network 410 may be embodied as any type of communication network capable of facilitating communication between the electrical stimulation system 400 and the analytics server 420 and/or other remote devices. As such, the network 410 may include one or more networks, routers, switches, computers, and/or other intervening devices. For example, the network 410 may be embodied as or otherwise include one or more cellular networks, telephone networks, local or wide area networks, publicly available global networks (e.g., the Internet), ad hoc networks, short-range communication links, or a combination thereof.

The analytics server 420 may be embodied as any type of device(s) capable of performing the functions described herein. It should be appreciated that the efficacy of neuromodulation technologies is affected by continuously changing treatment variables. Treatment variables may be device-specific (e.g., lead migration and impedance changes, stimulation paradigm, etc.), physiological (e.g., neurological conditioning or tolerance, scar tissue formation, plasticity, etc.), psychological (e.g., depression, etc.), disease state specific (e.g., progression, improvement, etc.) and/or patient dependent (e.g., height, weight, age, race, etc.). Moreover, these treatment variables generally change with time and may interact (stim*time interaction, long-term physiological changes, etc.).

In some embodiments, the inputs for a neural network or other machine learning algorithm used by the analytics server 420 may include one or more of adjusted electrical stimulation signatures, patient information, patient demographics, diagnosis information, electrode positioning, patient sensations, measures of treatment efficacy and/or outcomes (e.g., Pain Rating Scale scores), time of day, duration of treatment, time elapsed since start of treatment plan, and/or other machine learning model inputs. Further, in various embodiments, the analytics server 420 may utilize any machine learning and/or artificial intelligence algorithm for performing the functions described herein. For example, in some embodiments, the analytics server 420 may utilize one or more neural network algorithms, regression algorithms, instance-based algorithms, regularization algorithms, decision tree algorithms, Bayesian algorithms, clustering algorithms, association rule learning algorithms, deep learning algorithms, dimensionality reduction algorithms, and/or other suitable machine learning algorithms, techniques, and/or mechanisms.

It should be further appreciated that, although the analytics server 420 is described herein as a computing device outside of a cloud computing environment, in other embodiments, the analytics server 420 may be embodied as a cloud-based device or collection of devices within a cloud computing environment. Further, in cloud-based embodiments, the analytics server 420 may be embodied as a server-ambiguous computing solution, for example, that executes a plurality of instructions on-demand, contains logic to execute instructions only when prompted by a particular activity/trigger, and does not consume computing resources when not in use. That is, the analytics server 420 may be embodied as a virtual computing environment residing "on" a computing system (e.g., a distributed network of devices) in which various virtual functions (e.g., Lambda functions, Azure functions, Google cloud functions, and/or other suitable virtual functions) may be executed corresponding with the functions of the analytics server 420 described herein. For example, when an event occurs (e.g., data is transferred to the analytics server 420 for handling), the virtual computing environment may be communicated with (e.g., via a request to an API of the virtual computing environment), whereby the API may route the request to the correct virtual function (e.g., a particular server-ambiguous computing resource) based on a set of rules. For example, when a request for the transmission of data is made (e.g., via an appropriate user interface to the analytics server 420), the appropriate virtual function(s) may be executed to perform the actions before eliminating the instance of the virtual function(s).

Figure 12:
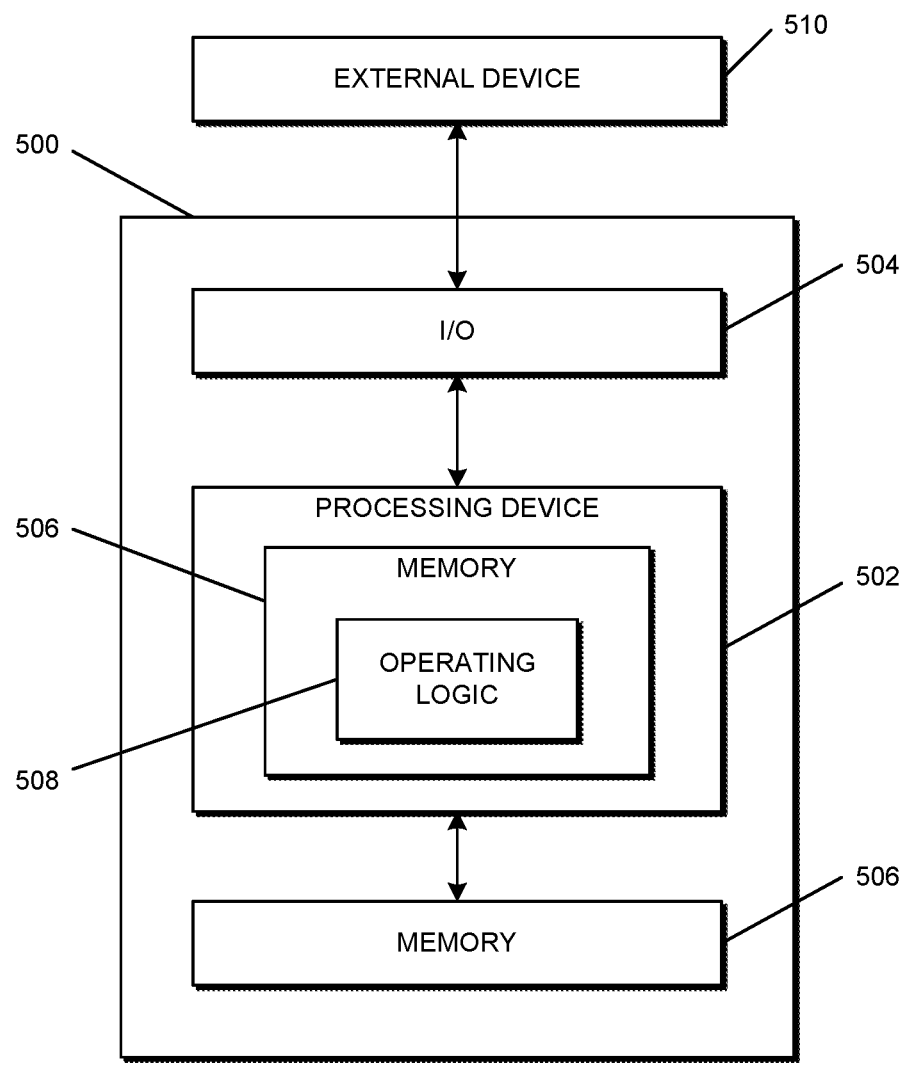
FIG. 12 is a simplified block diagram of at least one embodiment of a computing system.

Referring now to FIG. 12, a simplified block diagram of at least one embodiment of a computing device 500 is shown. The illustrative computing device 500 depicts at least one embodiment of a server that may be utilized in connection with the analytics server 420 illustrated in FIG. 12 and/or other devices in communication with the electrical stimulation system 400. Depending on the particular embodiment, the computing device 500 may be embodied as a server, desktop computer, laptop computer, tablet computer, notebook, netbook, Ultrabook™, mobile computing device, cellular phone, smartphone, wearable computing device, personal digital assistant, Internet of Things (IoT) device, processing system, router, gateway, and/or any other computing, processing, and/or communication device capable of performing the functions described herein.

The computing device 500 includes a processing device 502 that executes algorithms and/or processes data in accordance with operating logic 508, an input/output device 504 that enables communication between the computing device 500 and one or more external devices 510, and memory 506 which stores, for example, data received from the external device 510 via the input/output device 504.

The input/output device 504 allows the computing device 500 to communicate with the external device 510. For example, the input/output device 504 may include a transceiver, a network adapter, a network card, an interface, one or more communication ports (e.g., a USB port, serial port, parallel port, an analog port, a digital port, VGA, DVI, HDMI, Fire Wire, CAT 5, or any other type of communication port or interface), and/or other communication circuitry. Communication circuitry of the computing device 500 may be configured to use any one or more communication technologies (e.g., wireless or wired communications) and associated protocols (e.g., Ethernet, Bluetooth®, Wi-Fi®, WiMAX, etc.) to effect such communication depending on the particular computing device 500. The input/output device 504 may include hardware, software, and/or firmware suitable for performing the techniques described herein.

The external device 510 may be any type of device that allows data to be inputted or outputted from the computing device 500. For example, in various embodiments, the external device 510 may be embodied as the analytics server 420 and/or the electrical stimulation system 400. Further, in some embodiments, the external device 510 may be embodied as another computing device, switch, diagnostic tool, controller, printer, display, alarm, peripheral device (e.g., keyboard, mouse, touch screen display, etc.), and/or any other computing, processing, and/or communication device capable of performing the functions described herein. Furthermore, in some embodiments, it should be appreciated that the external device 510 may be integrated into the computing device 500.

The processing device 502 may be embodied as any type of processor(s) capable of performing the functions described herein. In particular, the processing device 502 may be embodied as one or more single or multi-core processors, microcontrollers, or other processor or processing/controlling circuits. For example, in some embodiments, the processing device 502 may include or be embodied as an arithmetic logic unit (ALU), central processing unit (CPU), digital signal processor (DSP), and/or another suitable processor(s). The processing device 502 may be a programmable type, a dedicated hardwired state machine, or a combination thereof. Processing devices 502 with multiple processing units may utilize distributed, pipelined, and/or parallel processing in various embodiments. Further, the processing device 502 may be dedicated to performance of just the operations described herein, or may be utilized in one or more additional applications. In the illustrative embodiment, the processing device 502 is programmable and executes algorithms and/or processes data in accordance with operating logic 508 as defined by programming instructions (such as software or firmware) stored in memory 506. Additionally or alternatively, the operating logic 508 for processing device 502 may be at least partially defined by hardwired logic or other hardware. Further, the processing device 502 may include one or more components of any type suitable to process the signals received from input/output device 504 or from other components or devices and to provide desired output signals. Such components may include digital circuitry, analog circuitry, or a combination thereof.

The memory 506 may be of one or more types of non-transitory computer-readable media, such as a solid-state memory, electromagnetic memory, optical memory, or a combination thereof. Furthermore, the memory 506 may be volatile and/or nonvolatile and, in some embodiments, some or all of the memory 506 may be of a portable type, such as a disk, tape, memory stick, cartridge, and/or other suitable portable memory. In operation, the memory 506 may store various data and software used during operation of the computing device 500 such as operating systems, applications, programs, libraries, and drivers. It should be appreciated that the memory 506 may store data that is manipulated by the operating logic 508 of processing device 502, such as, for example, data representative of signals received from and/or sent to the input/output device 504 in addition to or in lieu of storing programming instructions defining operating logic 508. As shown in FIG. 12, the memory 506 may be included with the processing device 502 and/or coupled to the processing device 502 depending on the particular embodiment. For example, in some embodiments, the processing device 502, the memory 506, and/or other components of the computing device 500 may form a portion of a system-on-a-chip (SoC) and be incorporated on a single integrated circuit chip.

In some embodiments, various components of the computing device 500 (e.g., the processing device 502 and the memory 506) may be communicatively coupled via an input/output subsystem, which may be embodied as circuitry and/or components to facilitate input/output operations with the processing device 502, the memory 506, and other components of the computing device 500. For example, the input/output subsystem may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations.

The computing device 500 may include other or additional components, such as those commonly found in a typical computing device (e.g., various input/output devices and/or other components), in other embodiments. It should be further appreciated that one or more of the components of the computing device 500 described herein may be distributed across multiple computing devices. In other words, the techniques described herein may be employed by a computing system that includes one or more computing devices. Additionally, although only a single processing device 502, I/O device 504, and memory 506 are illustratively shown in FIG. 12, it should be appreciated that a particular computing device 500 may include multiple processing devices 502, I/O devices 504, and/or memories 506 in other embodiments. Further, in some embodiments, more than one external device 510 may be in communication with the computing device 500.

As described above, the electrical stimulation system 400 is configured to pseudo-randomly deliver electrical stimuli through a set of electrodes in an electrode array 408 to neural and/or non-neural tissue, in order to more effectively treat acute/chronic pain and/or other medical conditions while avoiding neurological tolerance in the patient. An exemplary embodiment of the electrode array 408 is depicted and described in reference to FIG. 13.

Figure 13:
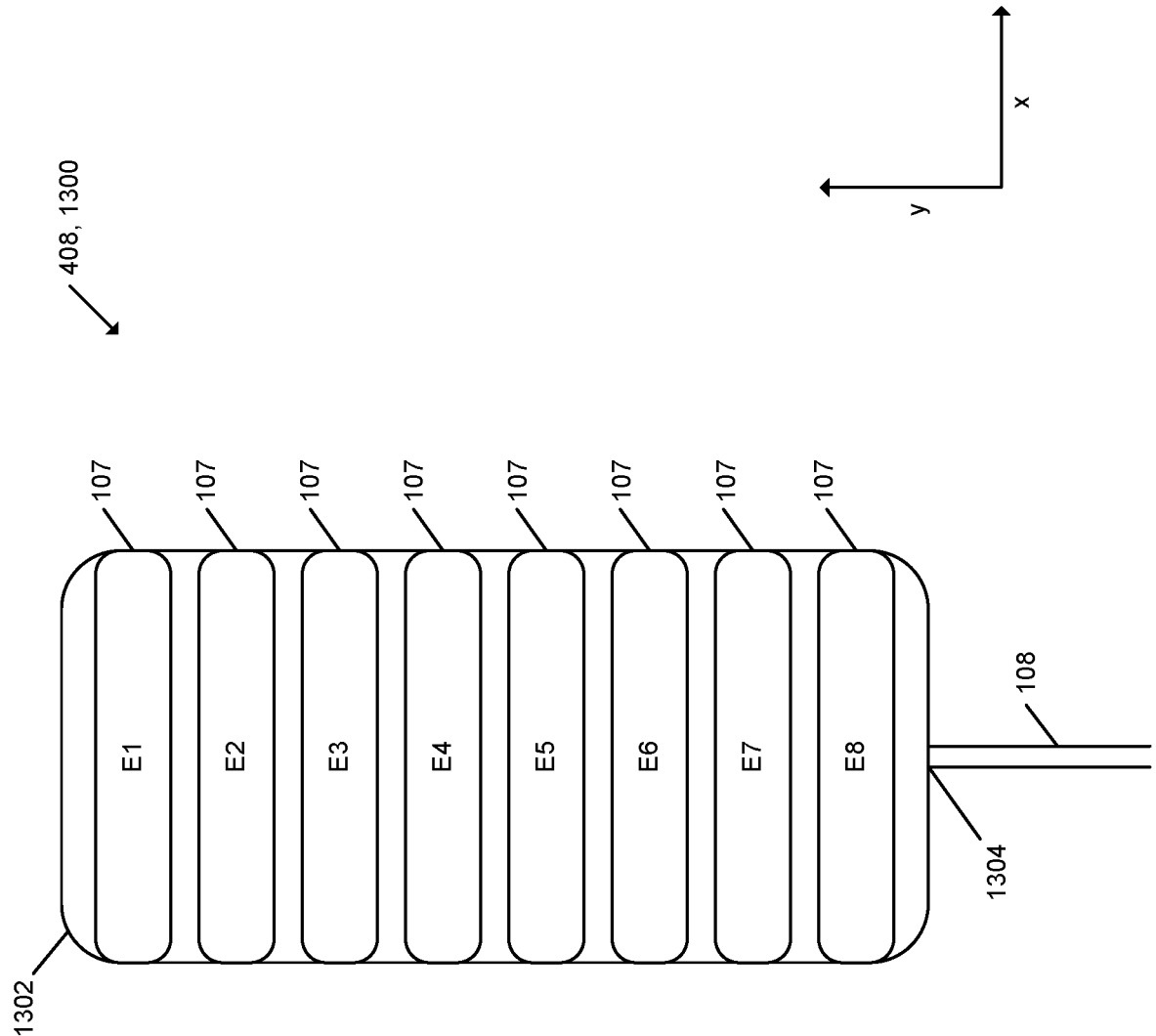
FIG. 13 illustrates at least one embodiment of an electrode array of an electrical stimulation device.

Referring now to FIG. 13, at least one embodiment of an electrode array 1300 is shown as part of an electrode assembly 1302. As shown, the illustrative electrode array 1300 includes eight electrodes 107, which are labeled as E1-E8 for convenience. Although the illustrative embodiment of the electrode array 1300 depicts eight electrodes 107, it should be appreciated that the electrode array 1300 may include a greater or lesser number of electrodes in other embodiments. It should be appreciated that the electrode array 1300 (or, more specifically, the electrodes 107 thereof) may be electrically coupled to a signal generator 109 through a lead 108 as described herein. As shown, in the illustrative embodiment, the electrode assembly 1302 is relatively rectangular in cross-sectional shape, extending lengthwise and distally from a point of connection 1304 with the lead 108 (e.g., along a y-axis). However, it should be appreciated that the electrode assembly 1302 may be otherwise shaped in other embodiments (e.g., cylindrical). In the illustrative embodiment, each of the electrodes 107 (i.e., E1-E8) extends laterally across the electrode assembly 1302 (e.g., along an x-axis) and is spatially separated from the other electrodes 107 (e.g., to avoid electrical interference between electrodes 107 and/or other unwanted electrical/ electromagnetic characteristics). In the illustrative embodiment, the E1 electrode 107 is depicted as the most distal electrode 107, and the E8 electrode 107 is depicted as the most proximal electrode 107. In other embodiments, however, it should be appreciated that the lead 108 may otherwise connect with the electrode assembly 1302.

In use, in some embodiments, the controller 110 of the electrical stimulation system 400 is configured to randomly select a set of one or more electrodes 107 (e.g., from E1-E8) to function as anodes and a separate set of one or more electrodes 107 (e.g., from E1-E8) to function as cathodes. It should be appreciated that the remaining electrodes 107 (e.g., from E1-E8) that have not been selected to function as anodes or cathodes may remain off or otherwise non-functioning. Further, in some embodiments, the number of electrodes 107 selected as anodes and/or the number of electrodes 107 selected as cathodes may also be randomly determined. It should be appreciated that the electrical stimulation system 400 may use any suitable combination of hardware, firmware, and/or software and/or any suitable algorithm or technique to perform the random selections described herein.

Figure 14:
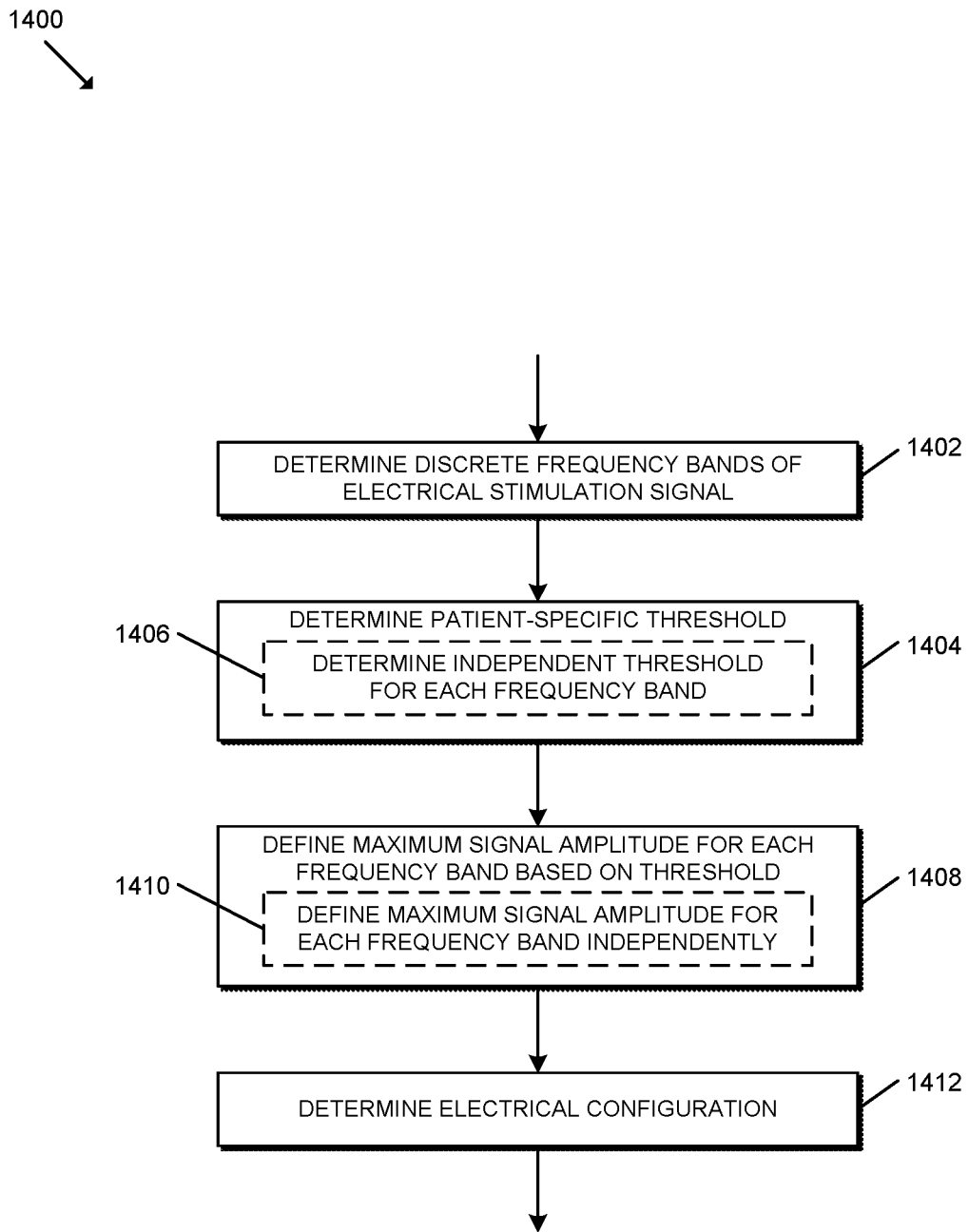
FIG. 14 is a simplified flow diagram of at least one embodiment of a method of calibrating an electrical stimulation system to a patient.

Referring now to FIG. 14, in use, the electrical stimulation system 400 may execute a method 1400 for calibrating an electrical stimulation system to a patient. It should be appreciated that the particular blocks of the method 1400 are illustrated by way of example, and such blocks may be combined or divided, added or removed, and/or reordered in whole or in part depending on the particular embodiment, unless stated to the contrary.

The illustrative method 1400 begins with block 1402 in which the electrical stimulation system 400 (e.g., the controller 110) determines the discrete frequency bands of the electrical stimulation signal to be used in conjunction with the technologies described herein. For example, in the illustrative embodiment, the electrical stimulation signal has a particular frequency range that is partitioned into discrete frequency bands, and data associated with those predefined discrete frequency bands may be stored in the memory 403 of the controller 110. In other words, in some embodiments, the electrical stimulation system 400 may determine the discrete frequency bands by retrieving the bounds or delimitations of those bands from the memory 403 of the controller 110. In an illustrative embodiment, the frequency range of the electrical stimulation signal is 0.0 kHz to 8.0 kHz, and the electrical stimulation system 400 utilizes eight discrete frequency bands that are linearly spaced (e.g., 0.0 kHz to 1.0 kHz, 1.0 kHz to 2.0 kHz, 2.0 kHz to 3.0 kHz, 3.0 kHz to 4.0 kHz, 4.0 kHz to 5.0 kHz, 5.0 kHz to 6.0 kHz, 6.0 kHz to 7.0 kHz, and 7.0 kHz to 8.0 kHz). In other embodiments, however, it should be appreciated that a different size of the frequency range, different number of discrete frequency bands, different size of discrete frequency bands, and/or different distribution of discrete frequency bands (e.g., logarithmically or octave distribution instead of linear distribution) may be stored and/or used by the controller 110. In another example embodiment, the electrical stimulation signal is a low frequency signal with a frequency range of 0.0 Hz to 1500 Hz, and the electrical stimulation system 400 utilizes ten discrete frequency bands that are linearly spaced (e.g., 0-150 Hz, 150-300 Hz, 300-450 Hz, 450-600 Hz, 600-750 Hz, 750-900 Hz, 900-1050 Hz, 1050-1200 Hz, 1200-1350 Hz, and 1350-1500 Hz). In another embodiment, the electrical stimulation system 400 utilizes discrete frequency bands that span both the low frequency range and the high frequency range, which may or may not be evenly spaced frequency bands. For example, one frequency band may be delimited by a lower frequency of 8 kHz and an upper frequency of 12 kHz, and another frequency band may be delimited by a lower frequency of 400 Hz and an upper frequency of 900 Hz. In the illustrative embodiment, the current amplitude and/or the voltage amplitude of the electrical stimulation signal outside of the frequency range (e.g., the range that is partitioned) is zero (or nominally zero). It should be appreciated that, in some embodiments, hardware and/or electrical characteristics may not enable the current amplitude and/or the voltage amplitude to be truly zero but merely a very small value that operates as though the value is essentially zero. In some embodiments, one of the discrete frequency bands may be 8-10 kHz, 7-8 kHz, and/or 4-5 kHz. It should be appreciated that the power of the electrical stimulation signal may be adjusted by adjusting the current and/or voltage of the signal. Accordingly, although various embodiments describe adjusting the current amplitude of the electrical stimulation signal, it should be appreciated that the electrical stimulation system 400 may, additionally or alternatively, adjust the voltage amplitude of the electrical stimulation signal in other embodiments. Similarly, although various embodiments describe adjusting, storing, and/or defining a maximum current amplitude, it should be appreciated that the electrical stimulation system 400 may, additionally or alternatively, adjust, store, and/or define a maximum voltage amplitude in other embodiments.

As described below in reference to the method 1500 of FIG. 15, the electrical stimulation system 400 determines multiple frequency band groupings, such that each of the frequency band groupings includes one or more discrete frequency bands. It should be appreciated that, in some embodiments, instead of the discrete frequency bands themselves being defined by the frequency delimitations described above, the frequency range of the frequency band groupings may be defined by those delimitations. For example, in an embodiment, one frequency band grouping may be delimited by a lower frequency of 8 kHz and an upper frequency of 12 kHz, and another frequency band grouping may be delimited by a lower frequency of 400 Hz and an upper frequency of 900 Hz. In other embodiments, one of the discrete frequency band groupings may have frequency delimitations of 8-10 kHz, 7-8 kHz, and/or 4-5 kHz.

In block 1404, the electrical stimulation system 400 (e.g., the controller 110) determines a patient-specific sensory threshold of the electrical stimulation signal for a particular patient to be treated. In particular, in block 1406, the electrical stimulation system 400 (e.g., the controller 110) may independently determine a patient-specific sensory threshold of the electrical stimulation signal for the particular patient for each discrete frequency band. For example, in some embodiments, the physician and/or patient may use an interface similar to the interface 1600 of FIG. 16 to independently adjust the current amplitude of the electrical stimulation signal within specific frequency bands. In particular, the physician or patient may increase the current amplitude of the electrical stimulation signal within a particular discrete frequency band (e.g., 0.0-1.0 kHz) by moving the indicator on the slide bar to the right up to a point at which the patient can feel a tingling or other sensation associated with the electrical stimulation signal. The electrical stimulation system 400 (e.g., the controller 110) may store that particular point (e.g., the current amplitude value) as the patient's sensory threshold for that particular frequency band. This process may be repeated for each of the other discrete frequency bands to identify the corresponding patient-specific sensory thresholds for the patient.

Figure 15:
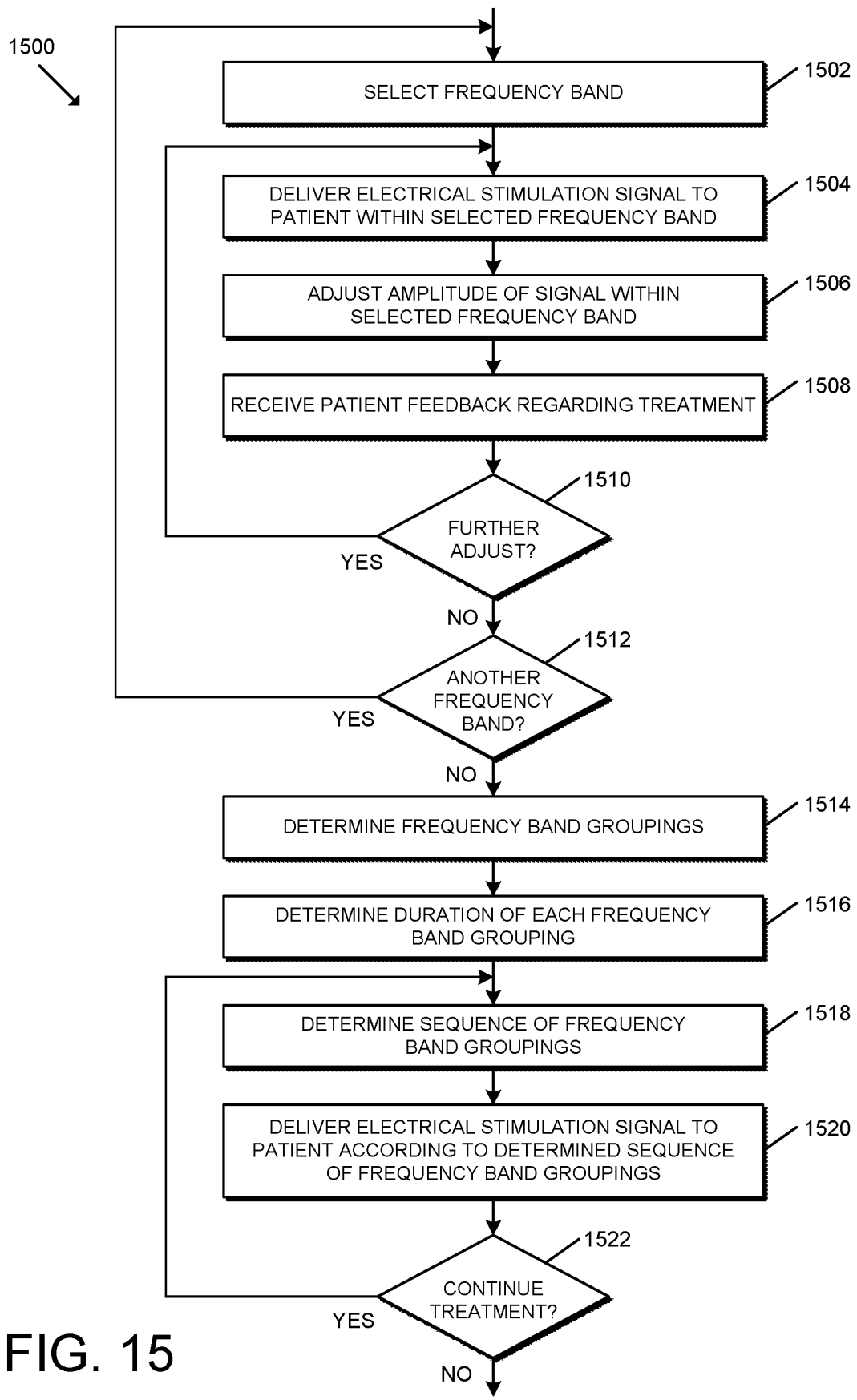
FIG. 15 is a simplified flow diagram of at least one embodiment of a method of rapid frequency cycling during electrical stimulation of a patient.
Figure 16:
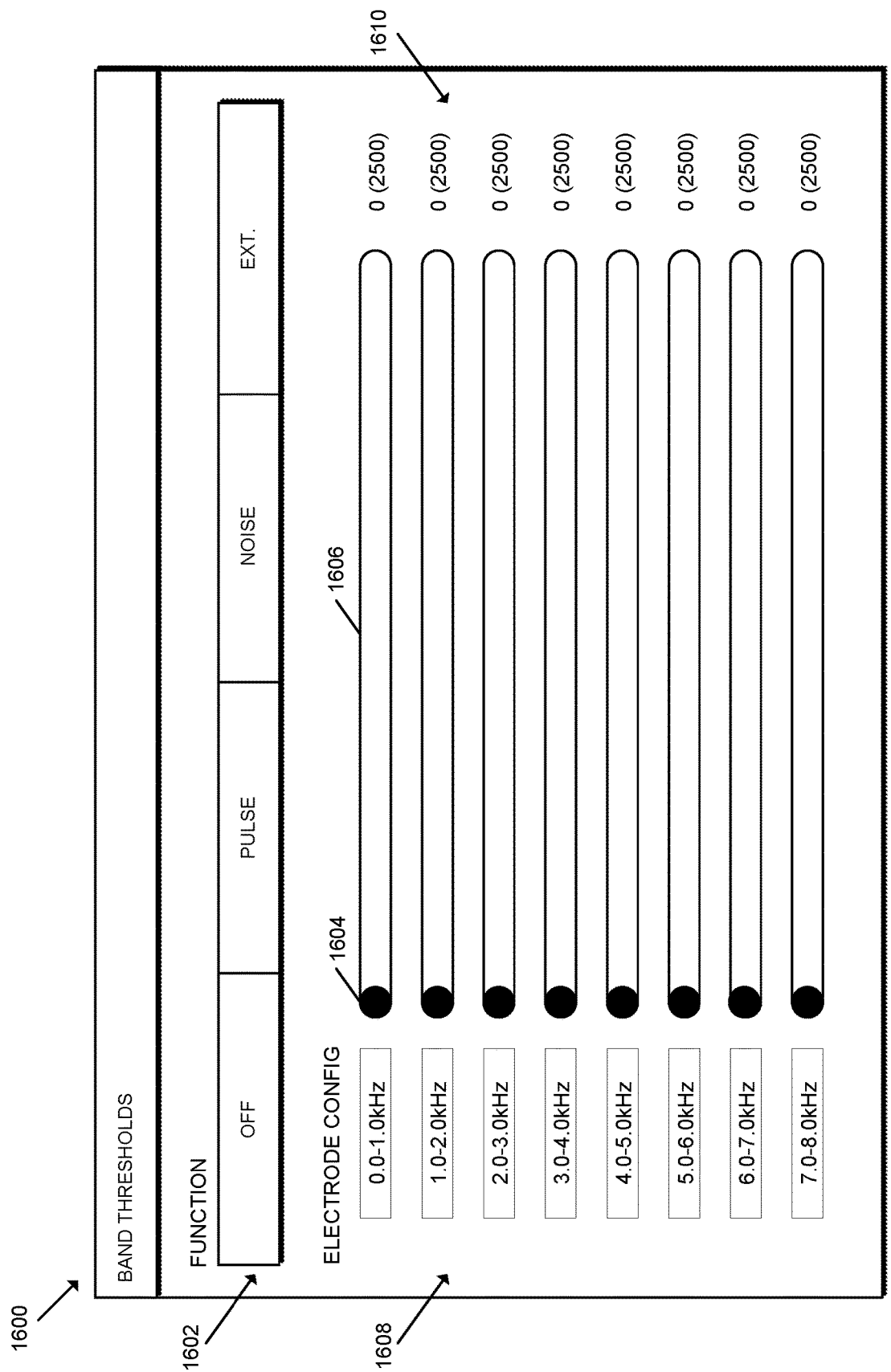
FIGS. 16-18 illustrate various user interfaces for configuring and calibrating an electrical stimulation system to a patient.

As shown in FIG. 16, the interface 1600 allows the physician or patient to select a corresponding electrical stimulation function (e.g., off, pulse, noise, external) by clicking one of the function labels 1602. The interface 1600 includes a moveable indicator 1604 on a slider bar 1606 that can be moved to the right or left to result in an increase or decrease, respectively, in the current amplitude of the electrical stimulation signal being delivered to the patient within the corresponding frequency band. As shown, each discrete frequency band includes a corresponding frequency band label 1608 and a corresponding value label 1610. The value label 1610 identifies the instantaneous value of the current amplitude for the corresponding frequency band along with the value that is currently saved in the memory 403 of the controller 110 in parentheses. In the illustrative embodiment, the instantaneous value can be saved for a particular frequency band by clicking on a particular frequency band label 1608. It should be appreciated that the interface 1600 provides an efficient and effective mechanism for determining and storing the patient-specific sensory thresholds for the patient. It should be further appreciated that similar features may be employed using a different set of interface components and/or display data. In some embodiments, an interface may be used to allow the patient to identify a location on in image or outline of a human body at which the patient is experiencing pain, which the electrical stimulation system 400 may use to determine the location at which to deliver the electrical stimulation signal. As described below in reference to the method 1500 of FIG. 15, the electrical stimulation system 400 determines multiple frequency band groupings, such that each of the frequency band groupings includes one or more discrete frequency bands. It should be appreciated that, in some embodiments, the frequency band groupings may be defined prior to determining a patient-specific sensory threshold such that the patient-specific sensory threshold may be determined relative to the frequency band groupings rather than the discrete frequency bands.

In block 1408, the electrical stimulation system 400 (e.g., the controller 110) defines a maximum current amplitude of the electrical stimulation signal based on the patient-specific sensory threshold. In particular, in block 1410, the electrical stimulation system 400 (e.g., the controller 110) may define an associated maximum current amplitude for each discrete frequency band independently (i.e., such that a maximum current amplitude is separately defined for each discrete frequency band). For example, the electrical stimulation system 400 is programmed to define the maximum current amplitude as 100-120% of the patient-specific sensory threshold depending on the particular embodiment. In particular, in some embodiments, the maximum current amplitude of a particular frequency band is defined as the same value as the patient-specific sensory threshold value stored in the memory 403 for that particular frequency band. In another embodiment, the maximum current amplitude of a particular frequency band is defined as a value that is 110% of the patient-specific sensory threshold value stored in the memory 403 for that particular frequency band. In yet another embodiment, the maximum current amplitude of a particular frequency band is defined as a value that is 120% of the patient-specific sensory threshold value stored in the memory 403 for that particular frequency band. It should be appreciated that by setting the maximum current amplitude at a number greater than the patient-specific sensory threshold value, but not substantially greater than that value, the patient is able to physically feel the electrical stimulation signal if desired by increasing the current amplitude value while also being limited from increasing the value so high that it could cause pain and/or nerve damage. Although described as being a pre-programmed value or percentage relative to the patient-specific sensory threshold value, it should be appreciated that the maximum current amplitude may be configured by the physician in other embodiments.

In block 1412, the electrical stimulation system 400 (e.g., the controller 110) determines an electrical configuration of the electrode array 408 (e.g., the electrode array 1300) to be used. More specifically, the electrical stimulation system 400 (e.g., the controller 110) may select a first set of electrical contacts of the electrode array 408 to operate as cathodes and a second set of electrical contacts of the electrode array 408 to operate as anodes. In some embodiments, the electrical stimulation system 400 may randomly determine the electrical configuration of the electrode array 408 periodically and/or aperiodically during treatment of the patient. In some embodiments, the electrical configuration may be defined by the physician and/or patient before and/or during treatment. For example, in some embodiments, the physician and/or patient may use an interface similar to the interface 1800 of FIG. 18 to select or define the electrical configuration of the electrode array 408. In particular, the physician or patient may select whether each electrode 107 of the electrode array 408 is positive, negative, or off, thereby defining whether the electrode 107 is a cathode, anode, or unused. The electrical stimulation system 400 (e.g., the controller 110) may store data associated with the electrical configuration.

Figure 18:
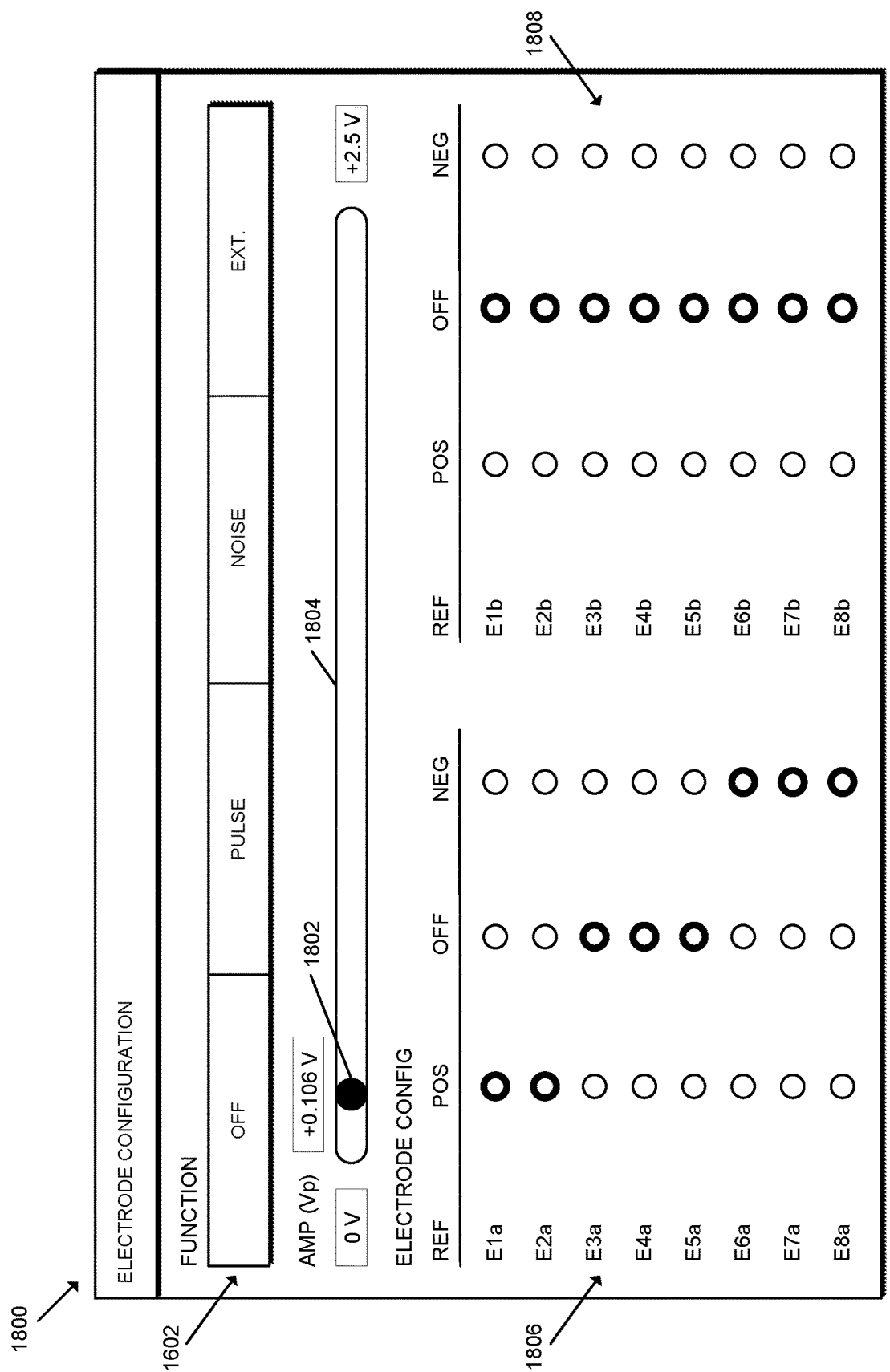

As shown in FIG. 18, the interface 1800 allows the physician or patient to select a corresponding electrical stimulation function (e.g., off, pulse, noise, external) by clicking one of the function labels 1602. The interface 1600 includes a moveable indicator 1802 on a slider bar 1804 that can be moved to the right or left to result in an increase or decrease, respectively, in the peak voltage of the electrical stimulation signal. The interface 1600 includes a set of electrode configuration options 1806 for a first lead and a set of electrode configuration options 1808 for a second lead, if a second lead is used. As shown, for each electrode, the electrode configuration options 1806, 1808 includes a reference identifier for the corresponding electrode (e.g., E1a) along with an option to configure the electrode to be positive, negative, or off. It should be appreciated that the interface 1800 provides an efficient and effective mechanism to predefining and storing one or more electrical configurations for the patient for initial and/or subsequent use during the patient's treatment. For example, in some embodiments, multiple electrical configurations may be stored, through which the electrical stimulation system 400 may sequentially or randomly toggle. It should be further appreciated that similar features may be employed using a different set of interface components and/or display data.

Although the blocks 1402-1412 are described in a relatively serial manner, it should be appreciated that various blocks of the method 1400 may be performed in parallel in some embodiments.

Referring now to FIG. 15, in use, the electrical stimulation system 400 may execute a method 1500 for rapid frequency cycling during electrical stimulation of a patient. It should be appreciated that the particular blocks of the method 1500 are illustrated by way of example, and such blocks may be combined or divided, added or removed, and/or reordered in whole or in part depending on the particular embodiment, unless stated to the contrary.

The illustrative method 1500 begins with block 1502 in which the electrical stimulation system 400 (e.g., the controller 110) selects a particular frequency band of the discrete frequency bands of the electrical stimulation signal for adjustment. In block 1504, the electrical stimulation system 400 (e.g., the signal generator 109 via instructions from the controller 110) delivers the electrical stimulation signal to the patient within the selected frequency band (e.g., while the other frequency bands have a current amplitude and/or voltage amplitude of nominally zero). In block 1506, the electrical stimulation system 400 adjusts the current amplitude and/or the voltage amplitude of the electrical stimulation signal within the selected frequency band, for example, by amplifying the current/voltage or attenuating the electrical stimulation signal within the selected frequency band. Although described throughout as involving the adjustment of the current/voltage amplitude, it should be appreciated that the phase may be adjusted, additionally or alternatively, in other embodiments. It should be appreciated that, in some embodiments, the physician and/or patient may interact with a user interface, such as the interface 1700 of FIG. 17, to cause the electrical stimulation system 400 to adjust the electrical stimulation signal. In block 1508, the electrical stimulation system 400 and/or the physician receives feedback regarding the treatment from the patient. It should be appreciated that the feedback can be provided by the patient, for example, based on self-report (e.g., introspection, observations of unwanted sensory—and/or motor activity, autonomic dysfunction, etc.), determined from data generated by sensors measuring physiological outcomes, based on data from artificial intelligence or machine learning systems (e.g., output or feedback data), or based on combinations thereof. For example, in the illustrative embodiment, the feedback from the patient may be provided by further adjustments made by the patient via the interface (e.g., the interface 1700).

In block 1510, the electrical stimulation system 400 (e.g., the controller 110) and/or the physician determines whether to further adjust the signal applied to the patient within the selected frequency band based on the patient feedback (e.g., in an effort to most optimally alleviate the patient's condition). If so, the method 1500 returns to block 1504 in which the electrical stimulation system 400 (e.g., via the signal generator 109) continues to deliver the electrical stimulation signal to the patient within the selected frequency band while the patient continues to adjust the electrical stimulation signal within the selected band. If the adjustments to the selected frequency band are completed, the method 1500 advances to block 1512 in which the electrical stimulation system 400 (e.g., the controller 110) selects another frequency band for further adjustment. If not, the method 1500 advances to block 1514.

It should be appreciated that blocks 1502-1512 of the method 1500 involve the independent tuning of the current/voltage amplitude of the electrical stimulation signal within each discrete frequency band based on feedback received from the patient. The physician and/or patient may adjust the corresponding current/voltage amplitude of the electrical stimulation signal within each discrete frequency band to a patient-selected point between zero and the maximum current/voltage amplitude (defined for the patient as described above) based on a reduction in pain and/or other symptoms physically experienced by the patient in real time. As indicated above, in some embodiments, a user interface similar to the user interface 1700 of FIG. 17 may be used by the physician and/or patient to do so. As described herein, the illustrative embodiment involves determining various frequency band groupings. As such, it should be appreciated that, in some embodiments, the electrical stimulation system 400 may independently tune each of the frequency band groupings rather than the discrete frequency bands, and therefore the frequency band groupings may be determined prior to tuning the electrical stimulation signal to the patient.

Figure 17:
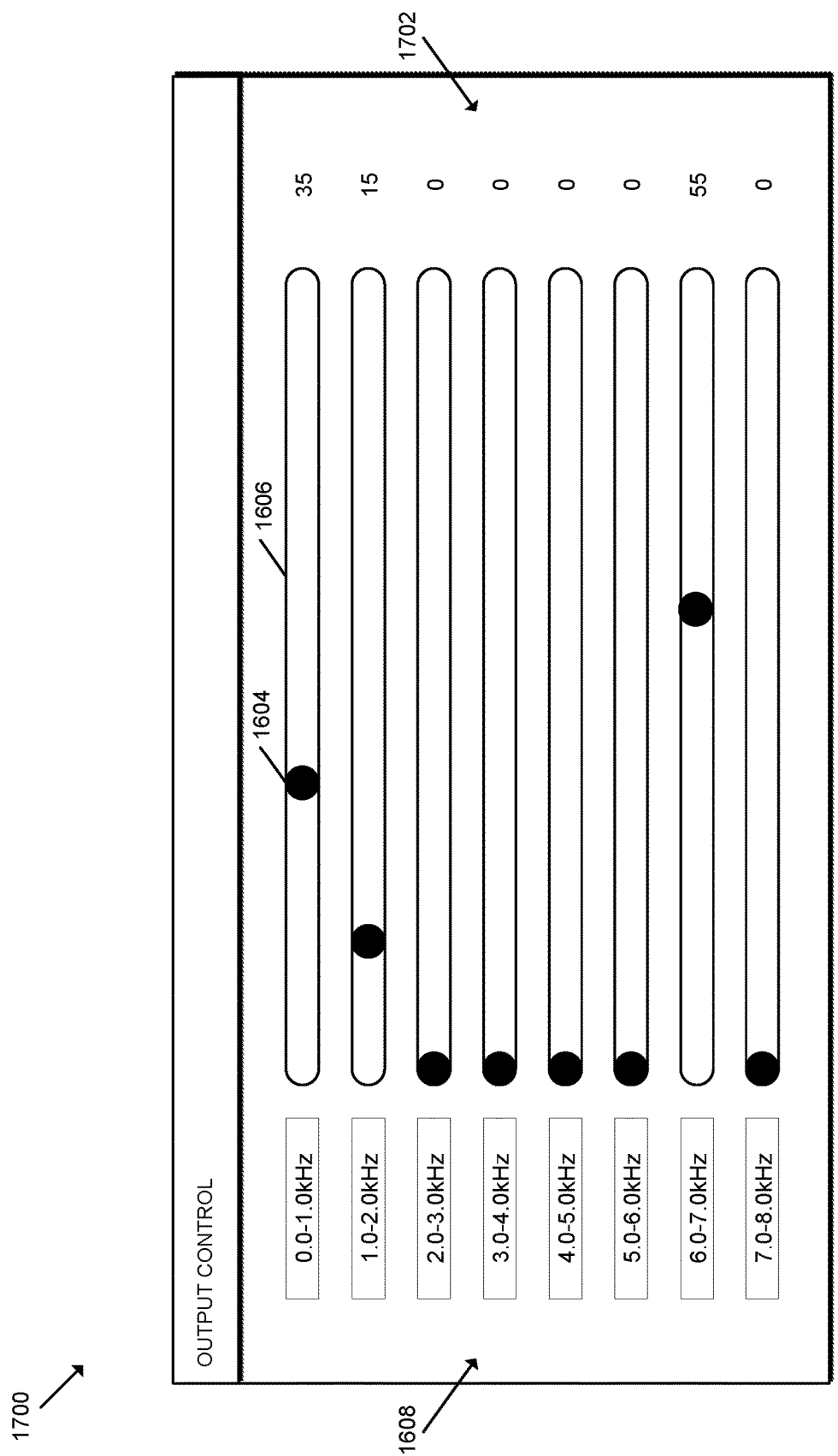

As shown in FIG. 17, the interface 1700 allows the physician or patient to adjust the current amplitude of the electrical stimulation signal between zero and the maximum current amplitude, which may be patient-specific and stored by the controller 110 as described in reference to the method 1400 of FIG. 14. The interface 1700 includes a moveable indicator 1604 on a slider bar 1606 that can be moved to the right or left to result in an increase or decrease, respectively, in the current amplitude of the electrical stimulation signal being delivered to the patient within the corresponding frequency band. As shown, each discrete frequency band includes a corresponding frequency band label 1608 and a corresponding label 1702 that identifies the instantaneous percentage of the maximum current amplitude at which the physician or patient has set the current amplitude value. It should be appreciated that the interface 1700 provides an efficient and effective mechanism for allowing the patient so define a point at which the patient's pain and/or other symptoms are alleviated. It should be further appreciated that similar features may be employed using a different set of interface components and/or display data.

Referring back to FIG. 15, in block 1514, the electrical stimulation system 400 (e.g., the controller 110) determines a plurality of frequency band groupings (or "bins") of the discrete frequency bands of the electrical stimulation signal. It should be appreciated that each frequency band grouping (or "bin") includes at least one discrete frequency band. For example, suppose the electrical stimulation system 400 utilizes discrete frequency bands that have 2 kHz bandwidths. One frequency band grouping may include a 0-2 KHz frequency band, another frequency band grouping may include a 2-4 kHz frequency band and 4-6 KHz frequency band, and yet another frequency band grouping may include a 6-8 KHz frequency band and 8-10 kHz frequency band. As such, it should be appreciated that the frequency band groupings may include a different number of frequency bands in some embodiments. In some embodiments, the frequency band groupings may be predefined and stored in the memory 403 of the controller 110, which in some embodiments may be configured by the physician. In other embodiments, the frequency band groupings may be randomly determined by the controller 110. In some embodiments, a particular frequency band is only able to be included in one of the frequency band groupings, whereas in other embodiments, a particular frequency band may be included in multiple frequency band groupings. In some embodiments, the electrical stimulation system 400 determines or defines four frequency band groupings. In other embodiments, the electrical stimulation system 400 determines or defines five frequency band groupings. In some embodiments, the electrical stimulation system 400 determines or defines six frequency band groupings. In yet other embodiments, the electrical stimulation system 400 may determine or define a different number of frequency band groupings.

In block 1516, the electrical stimulation system 400 (e.g., the controller 110) determines a corresponding duration that the electrical stimulation signal is delivered within each of the frequency band groupings (e.g., "bins" having the associated discrete frequency bands). For example, in some embodiments, the electrical stimulation system 400 may determine that the electrical stimulation signal is delivered within each of the frequency band groupings for two milliseconds. Depending on the particular embodiment, the electrical stimulation signal may be delivered within the frequency band groupings for the same or different amount of time. In some embodiments, the duration data may be predefined and stored in the memory 403 of the controller 110, which in some embodiments may be configured by the physician. In other embodiments, the corresponding duration that the electrical stimulation signal is delivered within each of the frequency band groupings may be randomly determined by the controller 110. In some embodiments, the electrical stimulation system 400 may determine to deliver the electrical stimulation signal within each of the frequency band groupings for a time selected from the range of 0.01 milliseconds to 10 minutes or, more specifically, 0.1 milliseconds to 10 seconds or 0.1 milliseconds to 5 seconds. It should be further appreciated that, in some embodiments, the electrical stimulation system 400 may also determine a pause duration indicative of an amount of idle time between delivering the electrical stimulation signal within two sequential frequency band groupings. In some embodiments, the pause duration between frequency band groupings may be selected from the range of 0.01 milliseconds to 10 minutes or, more specifically, 1 millisecond. Similarly, as described below, the electrical stimulation system 400 determines multiple sequences (or "songs") of frequency band groupings, and plays those "songs" sequentially. Accordingly, in some embodiments, the electrical stimulation system 400 may also determine a pause duration indicative of an amount of idle time between delivering the electrical stimulation signal via two sequential "songs." In some embodiments, the pause duration between "songs" may be selected from the range of 0.01 milliseconds to 10 minutes or, more specifically, 1 millisecond.

In block 1518, the electrical stimulation system 400 (e.g., the controller 110) determines a sequence (or "song") of the frequency band groupings. For example, in some embodiments, the electrical stimulation system 400 (e.g., the controller 110) may determine a random sequence of the frequency band groupings. In some embodiments, the electrical stimulation system 400 may store multiple predefined sequences of frequency band groupings, and determine the random sequence of frequency band groupings by randomly selecting one of the predefined sequences. In other embodiments, the entirety of the sequence may be randomly determined. In an illustrative embodiment, the electrical stimulation system 400 determines five sequences (or "songs") of the frequency band groupings; for example, in an embodiment including four frequency band groupings such as that described above, the electrical stimulation system 400 determines five different sequences of the four frequency band groupings.

In block 1520, the electrical stimulation system 400 (e.g., the signal generator 109 based on instructions received from the controller 110) generates and delivers the electrical stimulation signal through the electrode array 408 to the patient according to the determined sequence of frequency band groupings. As described above, it should be appreciated that the electrical stimulation signal delivered to the patient may be further based on the electrical configuration of the electrode array 408 (which may be predefined or randomly determined) and/or the duration of deliver of the electrical stimulation signal within each discrete frequency band grouping. As indicated above, the electrical stimulation signal may be a periodic pulse wave or, more specifically, a periodic pulse wave that has been adjusted as described herein. In block 1522, the electrical stimulation system 400 determines whether to continue treatment of the patient (e.g., based on a timer or other condition). If so, the method 1500 returns to block 1518 in which the electrical stimulation system 400 again determines a sequence (e.g., randomly) of frequency band groupings. In some embodiments, it should be appreciated that the electrical stimulation system 400 may also determine a new set of frequency band groupings, a duration of delivery of the signal within each frequency band grouping, the electrical configuration, and/ or other characteristics that serve to randomize or pseudo-randomize the electrical stimulation signal. In some embodiments, the electrical stimulation system 400 stores a set of predefined sequences (or "songs") of frequency band groupings (or "bins" of discrete frequency bands), such that the electrical stimulation system 400 cycles through the sequences (e.g., delivering the first sequence, then the second sequence, then the third sequence, then the fourth sequence, then back to the first sequence, then the second sequence, and so on). In other embodiments, the order of the predefined "songs" may be randomized when delivered in subsequent iterations. In yet other embodiments, the frequency band groupings included in the "songs" themselves may be randomized as described above.

Although the blocks 1502-1522 are described in a relatively serial manner, it should be appreciated that various blocks of the method 1500 may be performed in parallel in some embodiments.

What is claimed is:

1. A method of rapid frequency cycling during electrical stimulation, the method comprising:
   determining, by a controller of an electrical stimulation system, a plurality of frequency band groupings of discrete frequency bands of an electrical stimulation signal having a frequency range, wherein each frequency band grouping of the plurality of frequency band groupings includes at least one of the discrete frequency bands, wherein at least one of a corresponding current amplitude or a corresponding voltage amplitude of the electrical stimulation signal is independently tuned within each of a plurality of the discrete frequency bands based on feedback received by the controller;
   determining, by the controller, a random sequence of the frequency band groupings;
   generating, by at least one signal generator controlled by the controller, the electrical stimulation signal according to the determined random sequence of the frequency band groupings; and
   delivering the generated electrical stimulation signal through an electrode array to a patient to provide therapy to the patient.

2. The method of claim 1, further comprising determining, by the controller, a random electrical configuration of the electrode array by randomly selecting a first set of electrical contacts of the electrode array to operate as cathodes and a second set of electrical contacts of the electrode array, different from the first set of electrical contacts, to operate as anodes; and
   wherein delivering the electrical stimulation signal through the electrode array comprises delivering the electrical stimulation signal to the patient using the random electrical configuration of the electrode array.

3. The method of claim 2, further comprising repeatedly determining, by the controller, different random electrical configurations of the electrode array over the course of treatment of the patient.

4. The method of claim 1, wherein determining the random sequence of the frequency band groupings of the plurality of frequency band groupings comprises randomly selecting a predefined sequence of the frequency band groupings from a plurality of distinct predefined sequences of the frequency band groupings.

5. The method of claim 1, wherein the electrode array is positioned such that a distal electrical contact of the electrode array stimulates the patient's thoracic spine at T8 and a proximal electrical contact of the electrode array stimulates the patient's vertebral body at T10 to treat the patient for intractable leg and back pain.

6. The method of claim 1, further comprising:
   determining, by the controller, a patient-specific sensory threshold of the electrical stimulation signal for the patient;
   defining, by the controller, a maximum amplitude of the electrical stimulation signal based on the patient-specific sensory threshold;
   independently tuning, by the controller, the at least one of the corresponding current amplitude or the corresponding voltage amplitude of the electrical stimulation signal within each of the plurality of discrete frequency bands based on feedback received by the controller, where the patient adjusts the at least one of the corresponding current amplitude or the corresponding voltage amplitude of the electrical stimulation signal within each of the plurality of discrete frequency bands to a patient-selected point between zero and the maximum amplitude based on a reduction in pain physically experienced by the patient in real time.

7. The method of claim 6, wherein determining the patient-specific sensor threshold of the electrical stimulation signal comprises independently determining a corresponding patient-specific sensory threshold of the electrical stimulation signal for each of the plurality of discrete frequency bands; and
   wherein defining the maximum amplitude of the electrical stimulation signal comprises defining a corresponding maximum amplitude for each of the plurality of discrete frequency bands.

8. The method of claim 6, wherein defining the maximum amplitude of the electrical stimulation signal comprises defining the maximum amplitude as approximately 110% of the patient-specific sensory threshold.

9. The method of claim 1, wherein determining the plurality of frequency band groupings comprises determining the plurality of frequency band groupings based on an octave distribution.

10. The method of claim 1, wherein determining the plurality of frequency band groupings comprises determining the plurality of frequency band groupings based on a logarithmic distribution.

11. The method of claim 1, further comprising tuning the at least one of the corresponding current amplitude or the corresponding voltage amplitude associated with at least one of the discrete frequency bands based on feedback produced by one or more sensors associated with the patient.

12. The method of claim 1, further comprising determining a location at which to deliver the electrical stimulation signal based on an identification by the patient of a portion of a human body, represented in an image, where the patient experiences pain.

13. The method of claim 1, wherein determining the plurality of frequency band groupings comprises determining frequency band groupings that contain different quantities of discrete frequency bands.

14. The method of claim 1, wherein determining the plurality of frequency band groupings comprises determining frequency band groupings in which one discrete frequency band is present in two of the frequency band groupings.

15. The method of claim 1, further comprising determining, by the controller, a pause duration between delivery of sequential electrical stimulation signals corresponding to different frequency band groupings.

16. The method of claim 15, wherein determining the pause duration comprises selecting a pause duration between 0.1 milliseconds and 10 minutes.

17. A method of rapid frequency cycling during electrical stimulation, the method comprising:
   determining, by a controller of an electrical stimulation system, a plurality of frequency band groupings of discrete frequency bands of an electrical stimulation signal having a frequency range, wherein each of the frequency band groupings includes at least one of the discrete frequency bands, wherein at least one of a corresponding current amplitude or a corresponding voltage amplitude of the electrical stimulation signal is independently tuned within each of a plurality of the discrete frequency bands based on feedback received by the controller;
   determining, by the controller, a corresponding duration of delivery of the electrical stimulation signal within each frequency band grouping;
   determining, by the controller, a random electrical configuration of an electrode array of the electrical stimulation system by randomly selecting a first set of electrical contacts of the electrode array to operate as cathodes and a second set of electrical contacts of the electrode array, different from the first set of electrical contacts, to operate as anodes;
   determining, by the controller, a random sequence of the frequency band groupings;
   generating, by at least one signal generator controlled by the controller, the electrical stimulation signal according to the determined random sequence of the frequency band groupings and the determined corresponding duration of delivery of the electrical stimulation signal within each frequency band grouping; and
   delivering the generated electrical stimulation signal through the electrode array to a patient using the random electrical configuration of the electrode array to provide therapy to the patient.

18. The method of claim 17, wherein determining the plurality of frequency band groupings comprises determining frequency band groupings that contain different quantities of discrete frequency bands.

19. The method of claim 17, further comprising repeatedly determining, by the controller, different random electrical configurations of the electrode array over the course of treatment of the patient.

20. An electrical stimulation system for rapid frequency cycling during electrical stimulation, the system comprising:
   an electrode array;
   at least one signal generator coupled to the electrode array; and a controller electrically coupled to and configured to control the at least one signal generator, the controller having a processor and a memory comprising a plurality of instructions stored thereon that, in response to execution by the processor, causes the electrical stimulation system to:
determine, via the controller, a plurality of frequency band groupings of discrete frequency bands of an electrical stimulation signal having a frequency range, wherein each of the frequency band groupings includes at least one discrete frequency band, wherein at least one of a corresponding current amplitude or a corresponding voltage amplitude of the electrical stimulation signal is independently tuned within each of a plurality of the discrete frequency bands based on feedback received by the controller;
determine, via the controller, a random sequence of the frequency band groupings;
generate, via the at least one signal generator, the electrical stimulation signal according to the determined random sequence of the frequency band groupings; and
deliver, via the at least one signal generator, the generated electrical stimulation signal through the electrode array to a patient to provide therapy to the patient.

* * * * *